US008273871B2

(12) United States Patent
Hannon et al.

(10) Patent No.: US 8,273,871 B2
(45) Date of Patent: Sep. 25, 2012

(54) STRUCTURALLY DESIGNED SHRNAS

(75) Inventors: Gregory J. Hannon, Huntington, NY (US); Sihem Cheloufi, Boston, MA (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 13/252,784

(22) Filed: Oct. 4, 2011

(65) Prior Publication Data

US 2012/0021516 A1 Jan. 26, 2012

Related U.S. Application Data

(63) Continuation of application No. PCT/US2011/033615, filed on Apr. 22, 2011.

(60) Provisional application No. 61/327,510, filed on Apr. 23, 2010.

(51) Int. Cl.
*C12Q 1/68* (2006.01)
*C12P 19/34* (2006.01)
*C12N 15/63* (2006.01)
*C07H 21/02* (2006.01)
*C07H 21/04* (2006.01)

(52) U.S. Cl. ....... 536/24.5; 435/6; 435/91.1; 435/91.31; 435/455; 536/23.1; 536/24.3

(58) Field of Classification Search ............. 435/6, 91.1, 435/91.31, 455; 536/23.1, 24.5, 24.3
See application file for complete search history.

(56) References Cited

U.S. PATENT DOCUMENTS

| 7,750,144 B2 | 7/2010 | Zamore et al. |
| 7,851,452 B2 | 12/2010 | Gewirtz et al. |
| 2003/0180756 A1 | 9/2003 | Shi et al. |
| 2005/0008617 A1 | 1/2005 | Chen et al. |
| 2006/0223777 A1 | 10/2006 | Vermeulen et al. |
| 2008/0213861 A1 | 9/2008 | Hannon et al. |
| 2009/0004668 A1* | 1/2009 | Chen et al. ......................... 435/6 |
| 2009/0124566 A1 | 5/2009 | Chi et al. |
| 2009/0130751 A1* | 5/2009 | Davidson et al. .......... 435/320.1 |
| 2009/0281167 A1 | 11/2009 | Shen et al. |
| 2009/0306181 A1 | 12/2009 | Ikeda et al. |
| 2010/0112686 A1 | 5/2010 | Ge et al. |
| 2010/0221789 A1 | 9/2010 | Brown et al. |
| 2010/0286378 A1 | 11/2010 | Li et al. |
| 2011/0020816 A1 | 1/2011 | Chen et al. |
| 2011/0038849 A1 | 2/2011 | Xie et al. |
| 2011/0244562 A1* | 10/2011 | Davidson et al. .............. 435/325 |
| 2011/0269816 A1* | 11/2011 | Kaspar et al. ................ 514/44 A |

FOREIGN PATENT DOCUMENTS

| EP | 1614755 A1 | 1/2006 |
| JP | 2007-104969 A | 4/2007 |
| WO | WO 2008/095096 | 8/2008 |
| WO | WO 2008/124634 | 10/2008 |
| WO | WO 2009/076321 | 6/2009 |
| WO | WO 2010/011346 | 1/2010 |
| WO | WO 2011/008730 | 1/2011 |

OTHER PUBLICATIONS

Ge et al., RNA, vol. 16, pp. 106-117 (2010).*
Siolas et al., Nature Biotech., vol. 23, pp. 227-231 (2004).*
Tang et al, Nucleic Acids Res., vol. 21, No. 11, pp. 2729-2735 (1993).*
Siolas et al, Nature Biotech., vol. 23, pp. 227-331 (2004).*
Bosse and Simard, A new twist in the microRNA pathway: Not Dicer but Argonaute is required for a microRNA production. Cell Research, 2010, 20: 735-737.
Chang et al., Lessons from Nature: microRNA-based shRNA libraries. Nature Methods, 2006, 3(9):707-714.
Cheloufi et al., A Dicer-independent miRNA biogenesis pathway that requires Ago catalysis. Nature, 2010, 465:584-590.
Cheloufi and Hannon, Investigating the role of the argonautes during mouse embryogenesis. ABSTRACTS/Developmental Biology. 2007, Abstract #160, 306: p. 352.
Chong et al., Canonical and alternate functions of the microRNA biogenesis machinery. Genes Dev, 2010, 24:1951-1960.
Czech and Hannon, Small RNA sorting: matchmaking for Argonauts. Nature Reviews, 2011, 12:19-31.
Dickins et al., Probing tumor phenotypes using stable and regulated synthetic microRNA precursors. Nature Genetics, 2005, 37(11)1289-1295.
Diederichs and Haber, Dual Role for Argonautes in MicroRNA Processing and Posttranscriptional Regulation of MicroRNA Expression. Cell, 2007, 131:1097-1108.
Dueck and Meister, MicroRNA processing without Dicer. Genome Biology, 2010, 11:1-3.
Fellman et al., Functional Identification of Optimized RNAi Triggers Using a Massively Parallel Sensor Assay. Mol Cell, 2011, 41:733-746.
Gottwein and Cullen, Protocols for Expression and Functional Analysis of Viral MicroRNAs. Methods in Enzymology, 2007, Chapter 13, vol. 427, pp. 229-243.
Murchison et al., Characterization of Dicer-deficient murine embryonic stem cells. PNAS, 2005, 102(34):12135-12140.
Nelson et al., A novel monoclonal antibody against human Argonaute proteins reveals unexpected characteristics if miRNAs in human blood cells. RNA, 2007, 13:1787-1792.

(Continued)

*Primary Examiner* — Jane Zara
(74) *Attorney, Agent, or Firm* — Gary J. Gershik; Cooper & Dunham LLP

(57) ABSTRACT

Provided is an improved design of shRNA based on structural mimics of miR-451 precursors. These miR-451 shRNA mimics are channeled through a novel small RNA biogenesis pathway, require AGO2 catalysis and are processed by Drosha but are independent of DICER processing. This miRNA pathway feeds active elements only into Ago2 because of its unique catalytic activity. These data demonstrate that this newly identified small RNA biogenesis pathway can be exploited in vivo to produce active molecules.

20 Claims, 22 Drawing Sheets

OTHER PUBLICATIONS

Pase et al., miR-451 regulates zebrafish erythroid maturation in vivo via its target gata2. Blood, 2009, 113:1794-1804.

Patrick et al., Defective erythroid differentiation in miR-451 mutant mice mediated by 14-3-3ζ. Genes Dev, 2010, 24:1614-1619.

Premsrirut et al., A Rapid and Scalable System for Studying Gene Function in Mice Using Conditional RNA Interference. Cell, 2011, 145: 145-158.

Rasmussen et al., The miR-144/451 locus is required for erythroid homeostasis. J Exp Med, 2010, 207(7):1351-1358.

Siolas et al., Synthetic shRNAs as potent RNAi triggers. Nature Biotechnology, 2005, 23(2):227-231.

Wan and Chang, HOTAIR: Flight of noncoding RNAs in cancer metastasis. Cell Cycle, 2011, 9:3391-3392.

Yang and Lai, Dicer-independent, Ago2-mediated microRNA biogenesis in vertebrates. Cell Cycle, 2010, 9(22):4455-4460.

Yang et al., Conserved vertebrate mir-451 provides a platform for Dicer-independent, Ago2-mediated microRNA biogenesis. PNAS, 2010, 107: (34) :15163-15168.

Yu et al., miR-451 protects against erythroid oxidant stress by repressing 14-3-3ζ. Genes Dev, 2010, 24:1620-1633.

Ge et al., (2009) "Minimal-length short hairpin RNAs: The relationship of structure and RNAi activity.", *RNA* 16: 106-117.

Ge et al., (2009) "Effects of chemical modification on the potency, serum stability, and immunostimulatory properties of short shRNAs.", *RNA* 16:118-130.

McManus et al., (2002) "Gene silencing using micro-RNA designed hairpins.", *RNA* 8:842-850.

International Search Report and the Written Opinion of the International Searching Authority, issued Mar. 23, 2012 in connection with PCT International Application No. PCT/US2011/033615.

* cited by examiner

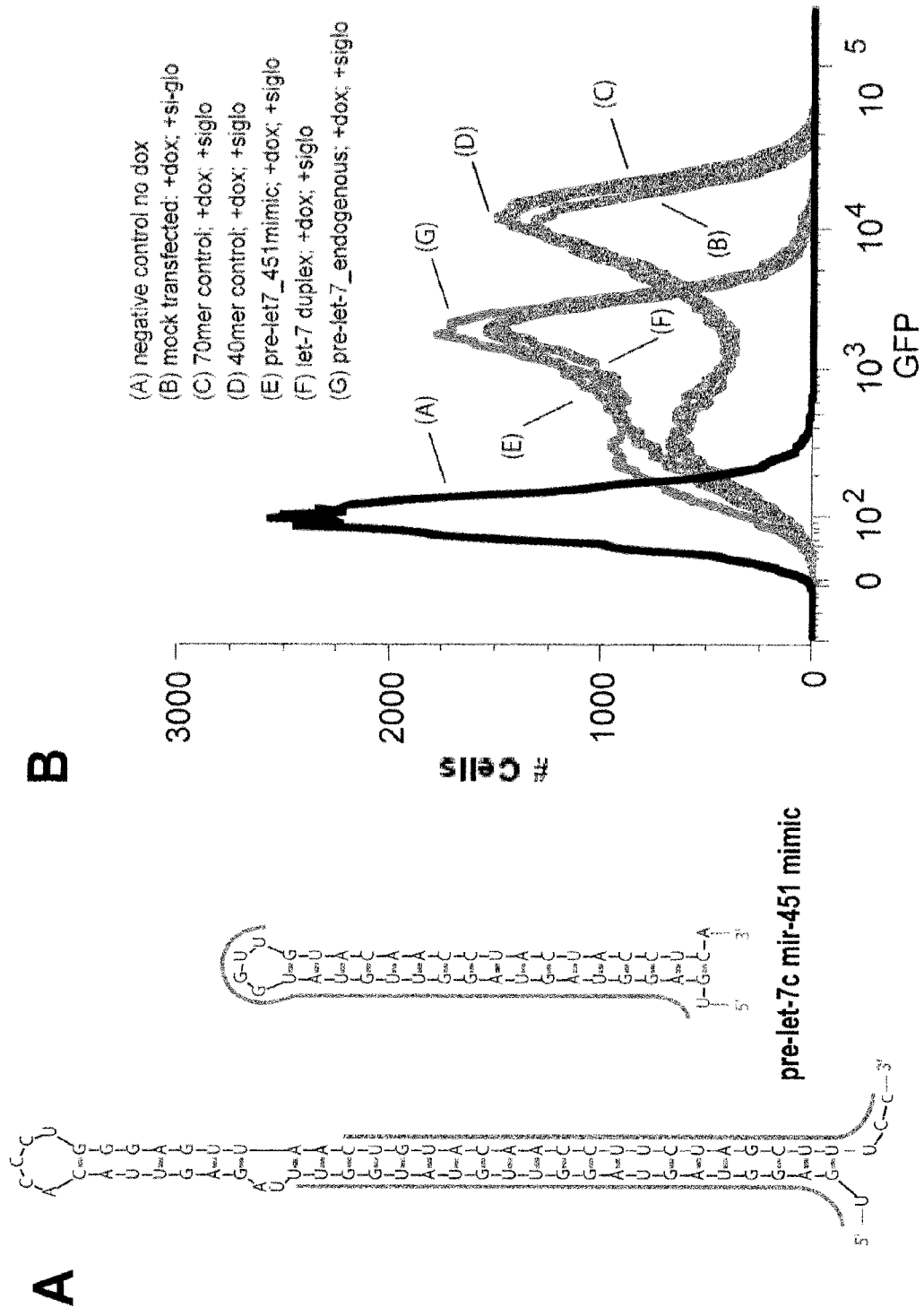
FIG. 1A-B

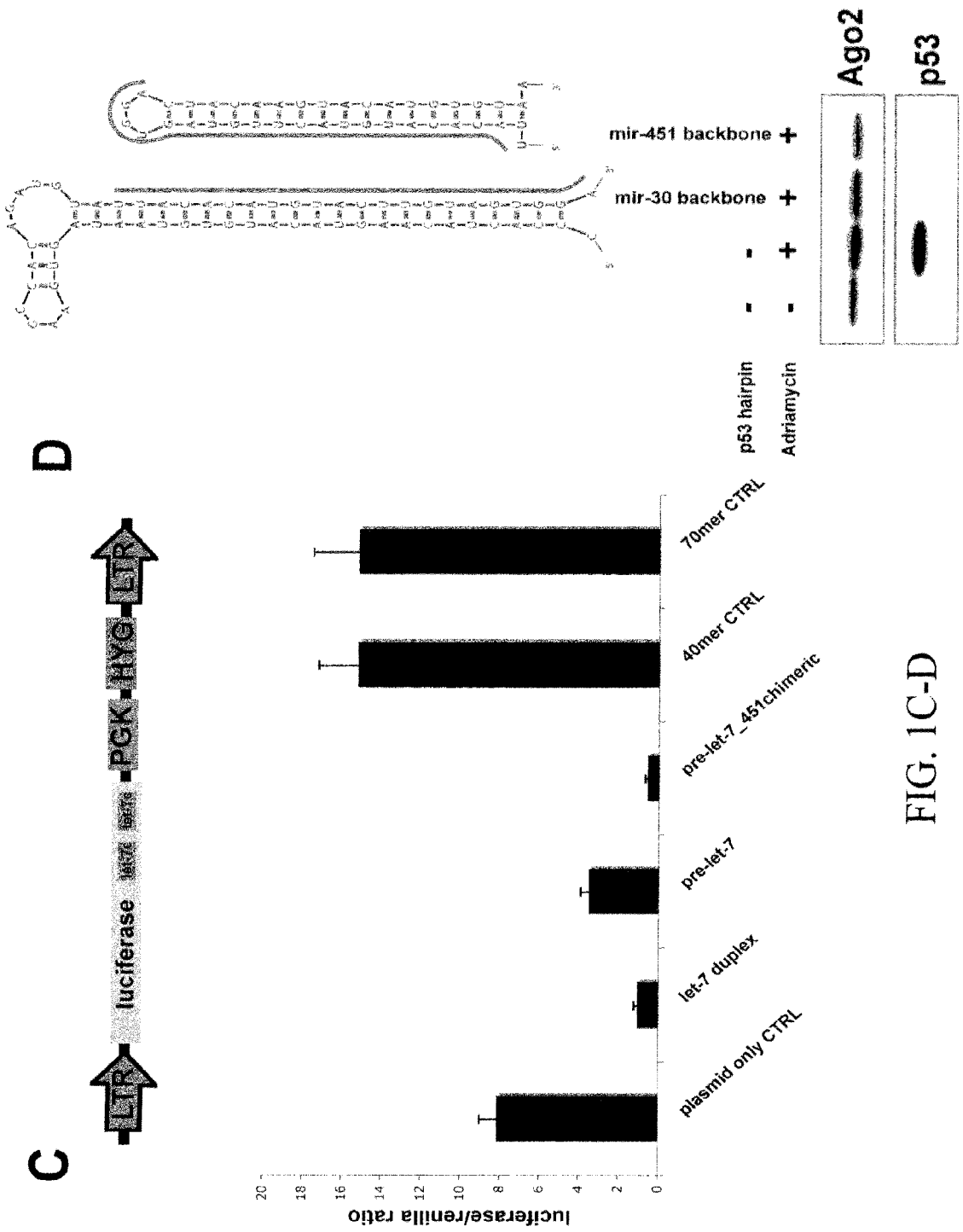
FIG. 1C-D a
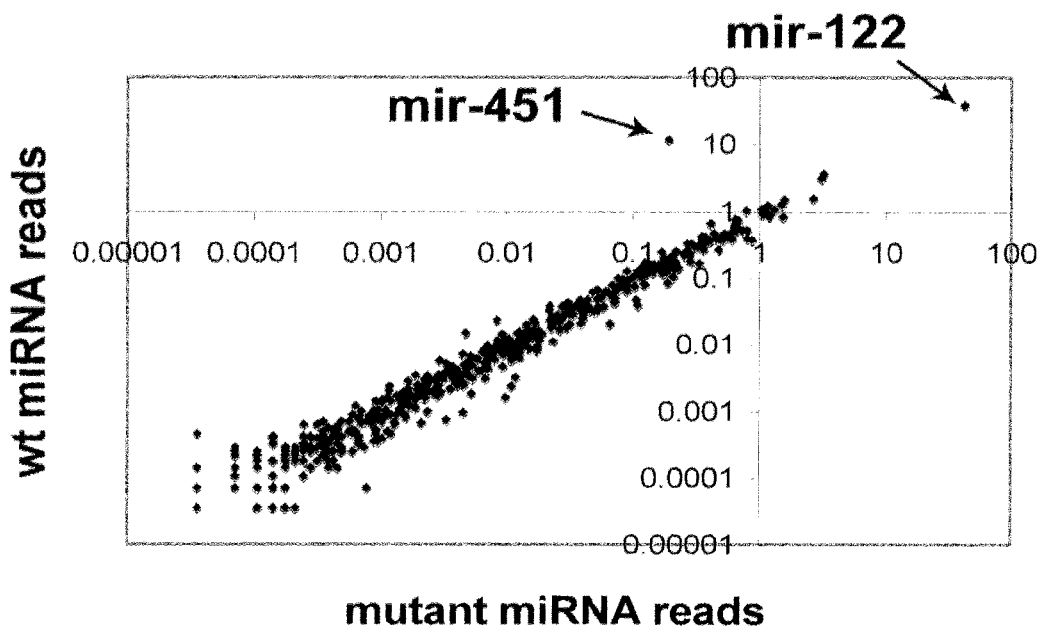
b
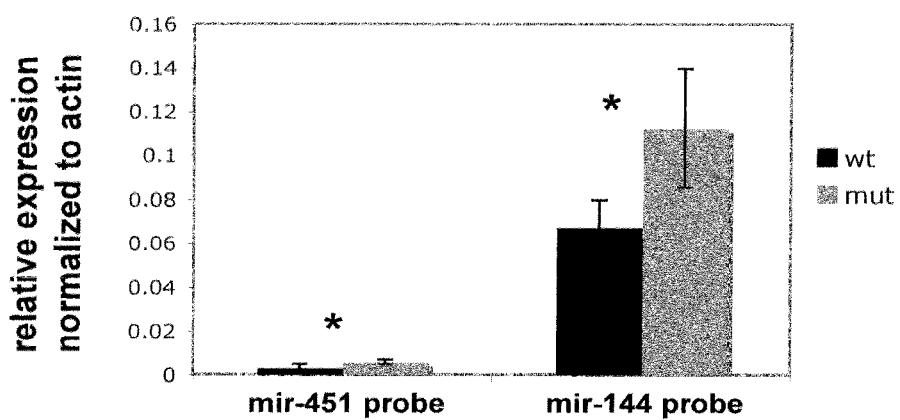
FIG. 4A-B

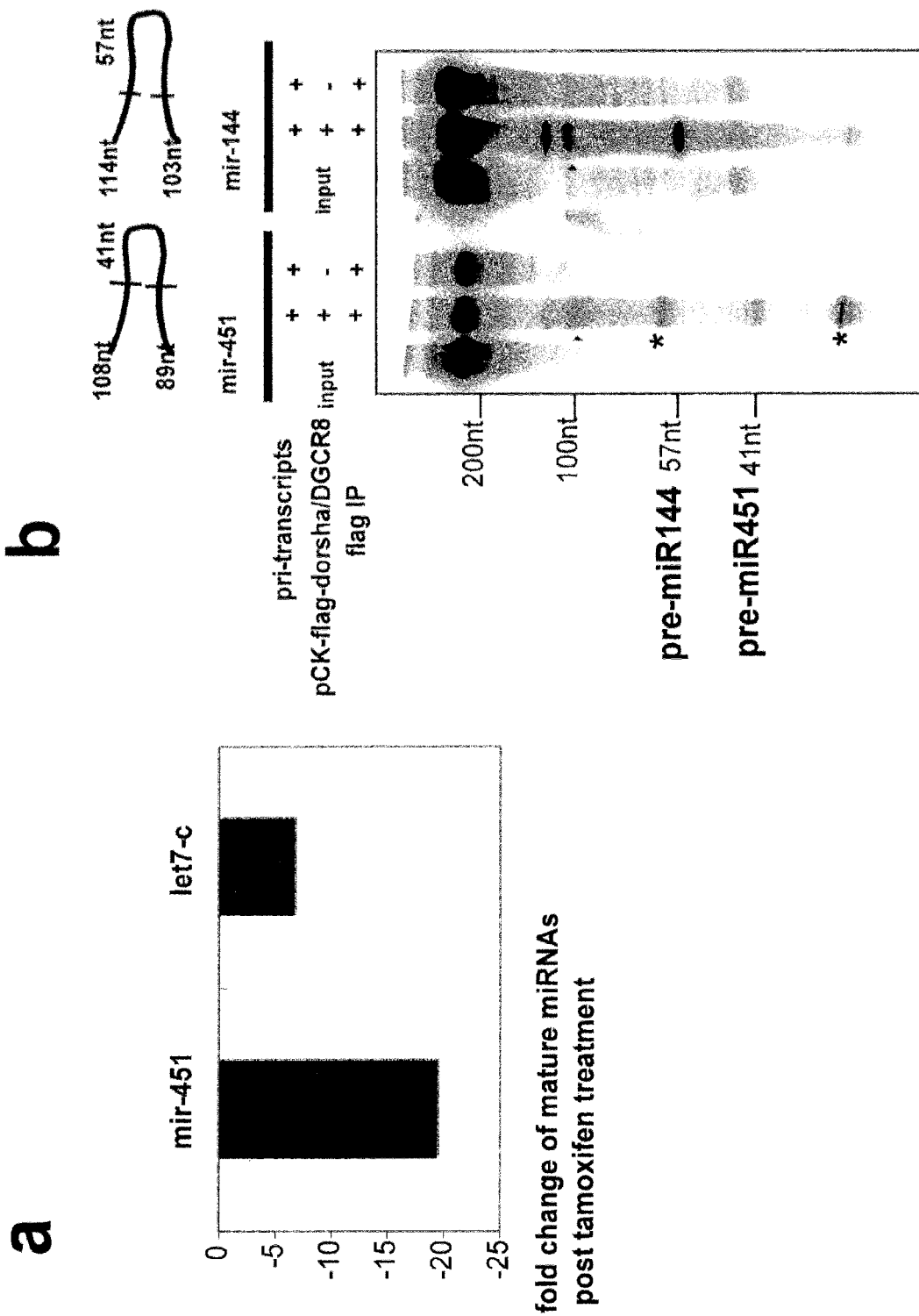
FIG. 5 A-B

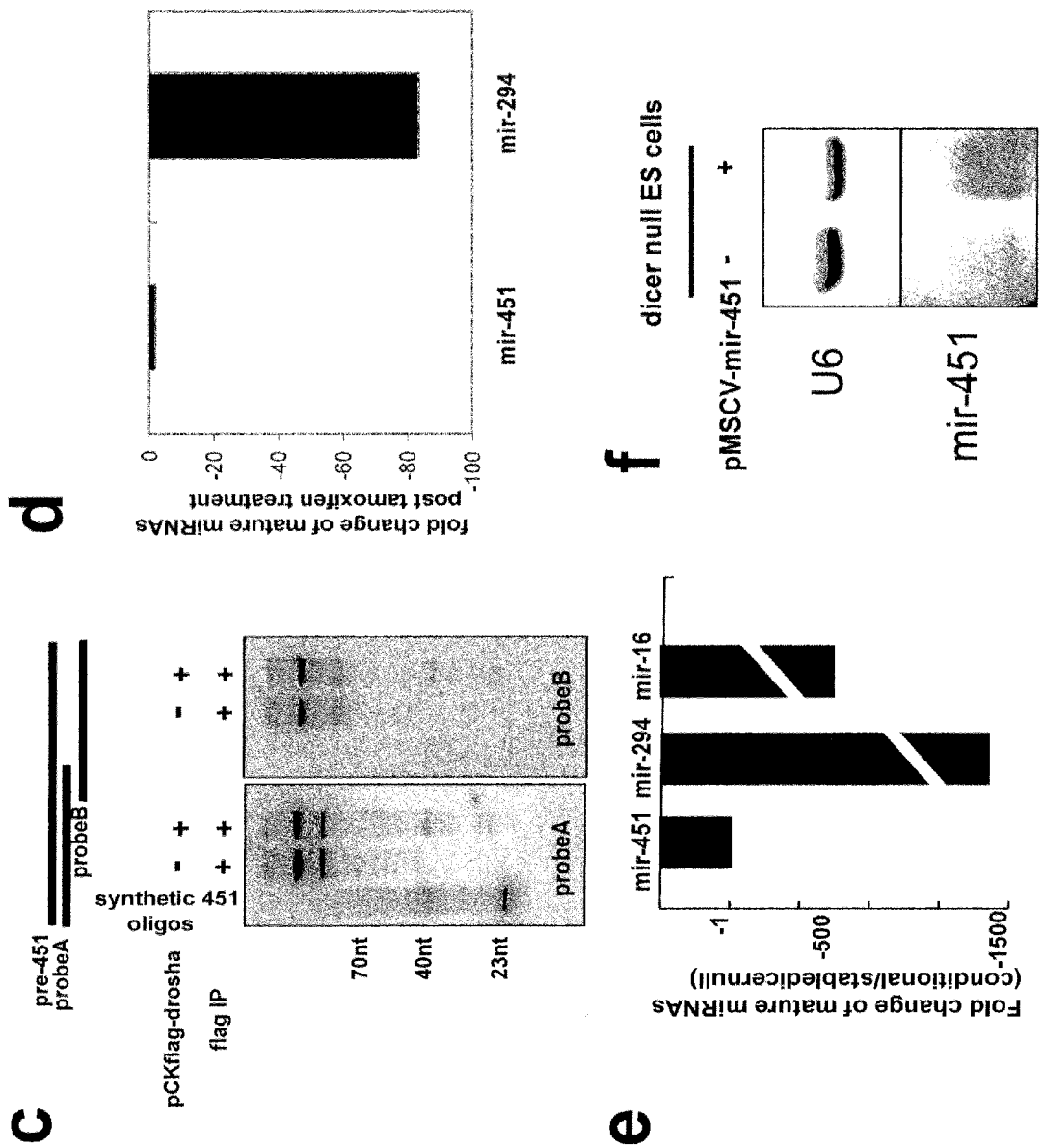
FIG. 5 C-F

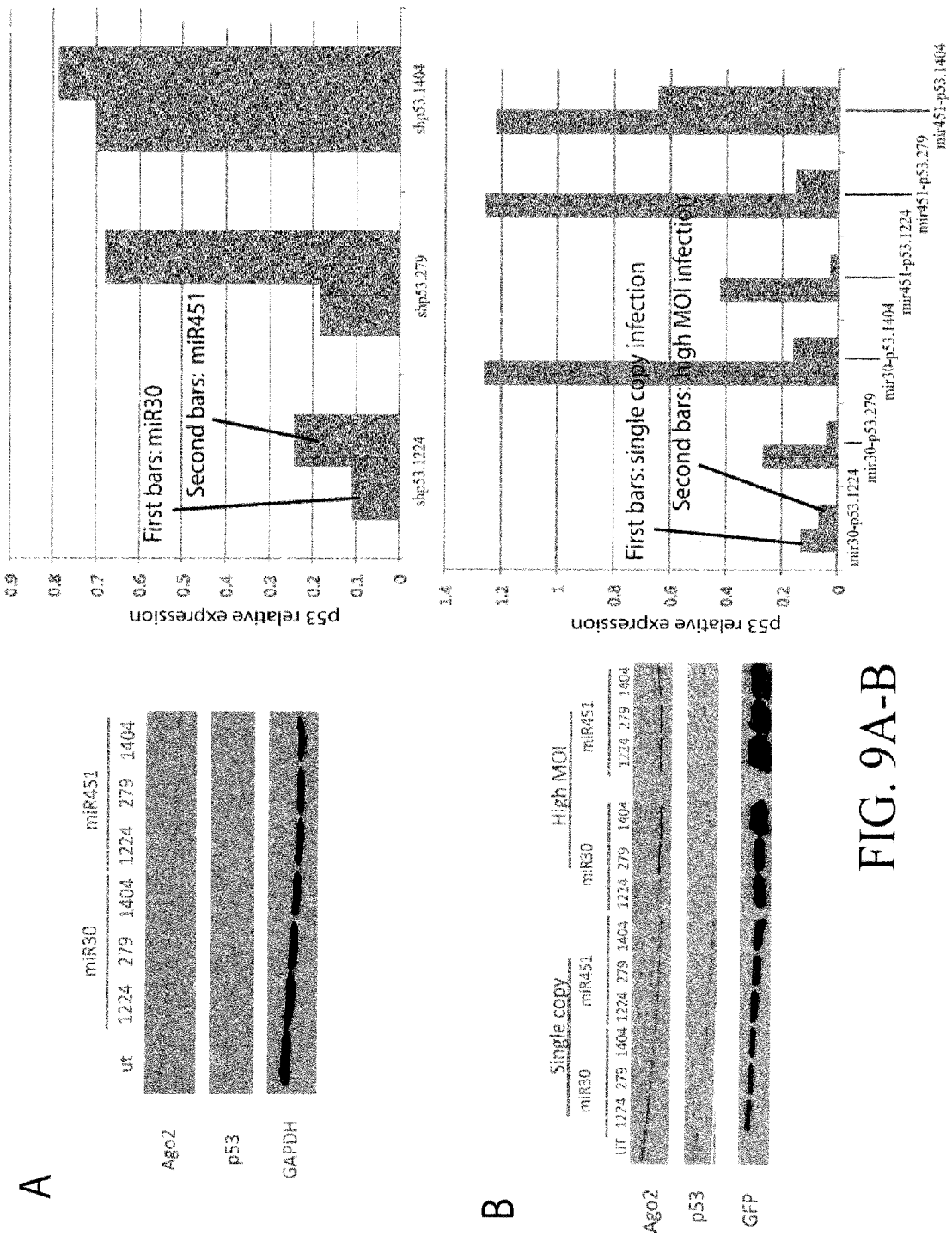
FIG. 9A-B

C
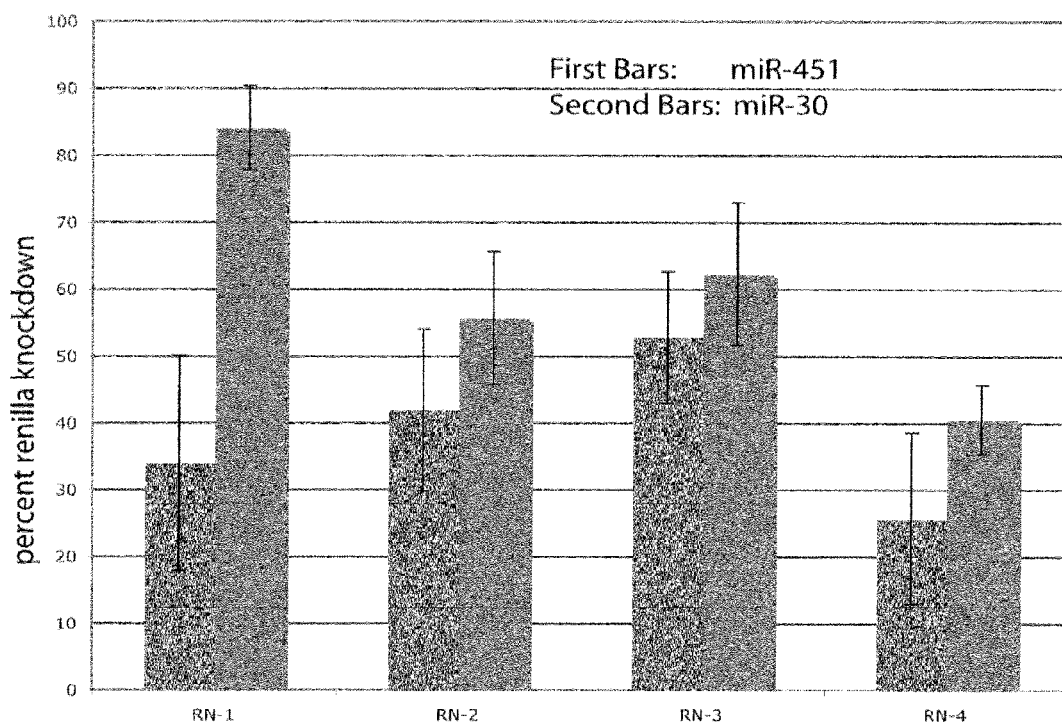
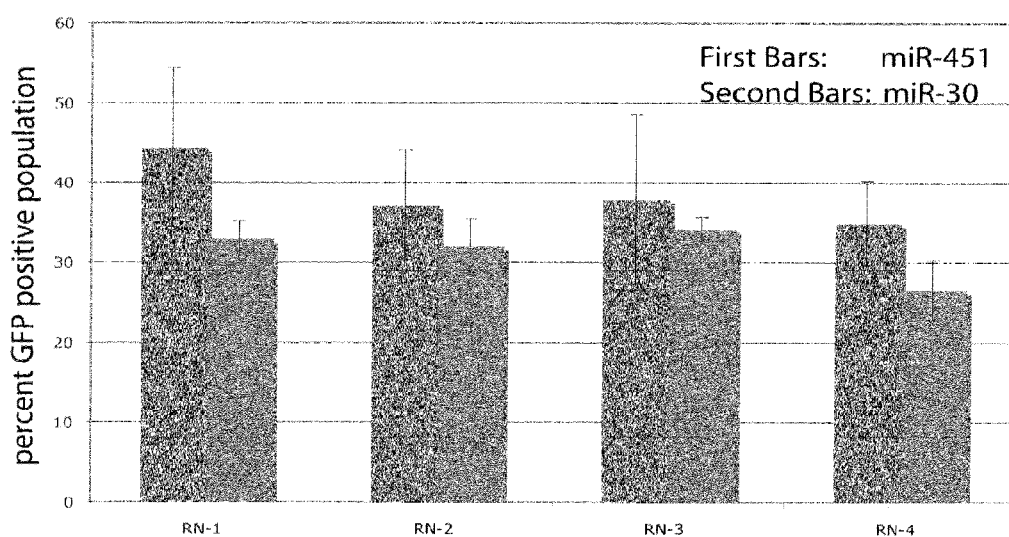
FIG. 9C

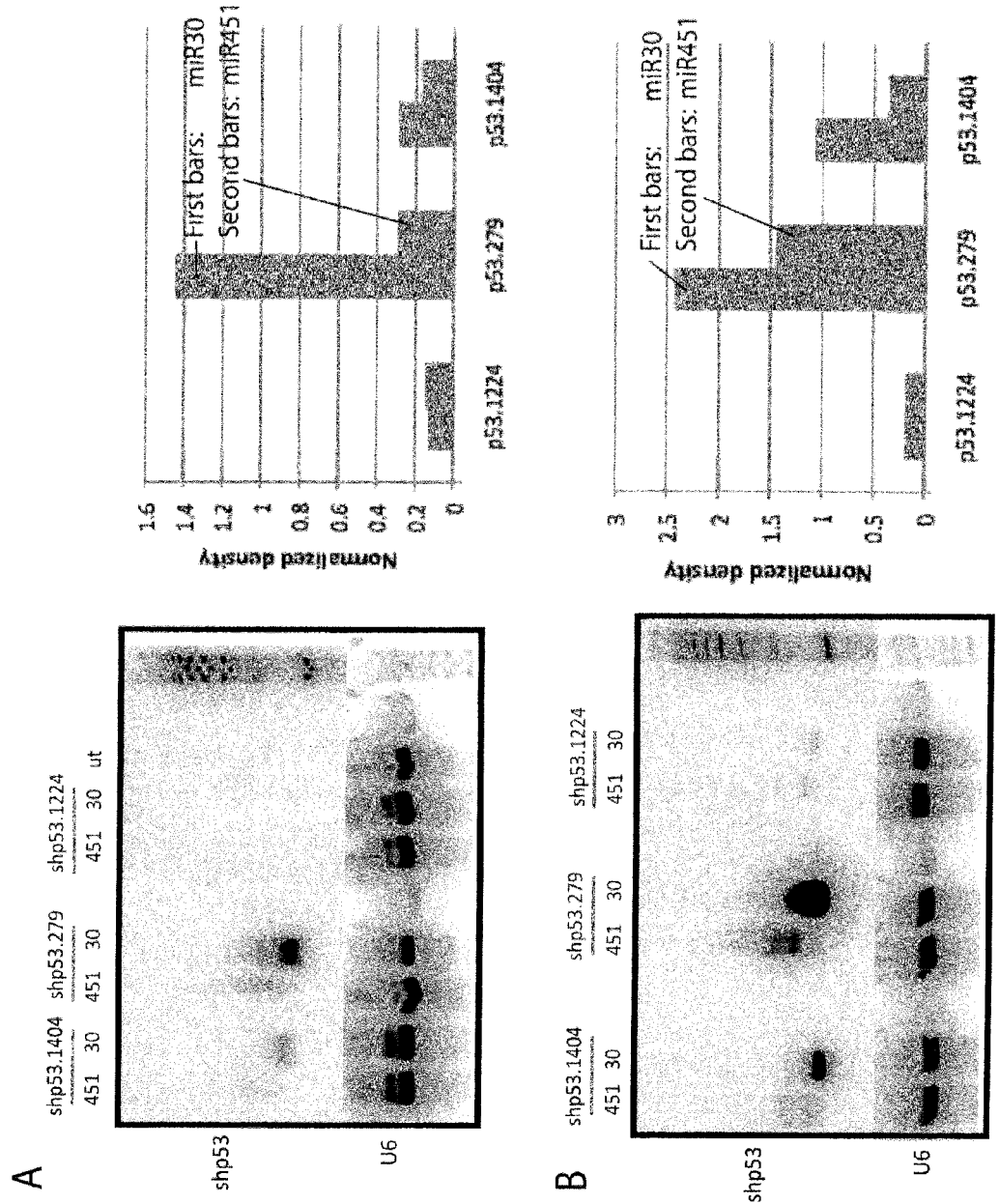
FIG. 10 A-B

STRUCTURALLY DESIGNED SHRNAS

This application is a continuation of PCT International Application No. PCT/US2011/033615, filed Apr. 22, 2011, claiming priority of U.S. Provisional Application No, 61/327, 510, filed Apr. 23, 2010, and designating the United States, the contents of which are hereby incorporated by reference.

This application incorporates-by-reference nucleotide and/or amino acid sequences which are present in the file named "111004_5981_82764_A_SEQUENCELISTING_GJG_REB.TXT", which is 8 kilobytes in size, and which was created Oct. 4, 2011 in the IBM-PC machine format, having an operating system compatibility with MS-Windows, which is contained in the text file filed Oct. 4, 2011 as part of this application.

This patent disclosure contains material which is subject to copyright protection, the copyright owner has no objection to the facsimile reproduction by anyone of the patent document or the patent disclosure, as it appears in the U.S. Patent and Trademark Office patent file or records, but otherwise reserves any and all copyright rights.

Throughout this application, patent applications, published patent applications, issued and granted patents, texts, and literature references are cited. For the purposes of the United States and other jurisdictions that allow incorporation by reference, the disclosures of these publications are incorporated by reference into this application.

1. BACKGROUND OF THE INVENTION

This invention relates in part to improvements directed to use of RNA interference (RNAi) technology that exploits a newly identified small RNA biogeneisis pathway.

Traditional RNAi technology in mammals takes advantage of the canonical microRNA (miRNA) pathway. Starting with PolII transcribed precursor RNAs, the biogenesis pathway involves two steps: DROSHA/DGCR8 cleaves the precursor transcript into a short hairpin RNA that is exported into the cytoplasm and then processed by DICER RNAseIII enzyme to yield a mature small (21-22 nt) RNA duplex, that is then loaded into one of four Argonaute proteins (AGO1 through AGO4) to form an active RNA Induced Silencing Complex (RISC). The conventional endogenous RNAi pathway therefore comprises three RNA intermediates: a long, largely single-stranded primary miRNA transcript (pri-mRNA); a precursor miRNA transcript having a stem-and-loop structure and derived from the pri-mRNA (pre-miRNA); and a mature miRNA.

Argonaute proteins are the key effectors of small RNA-mediated regulatory pathways that modulate gene expression, regulate chromosome structure and function, and provide an innate immune defense against viruses and transposons (Hutvagner, G. & Simard, M. J. *Nat Rev Mol Cell Biol* 9, 22-32 (2008)). The structure of Ago proteins is well conserved, consisting of an amino-terminal domain, the mid domain, and their signature PAZ and Piwi domains. Structure-function relationships in this family are becoming increasingly well understood (Joshua-Tor, L. *Cold Spring Harb Symp Quant Biol* 71, 67-72 (2006)). The PAZ and Mid domains help to anchor the small RNA guide, with PAZ binding the 3' end using a series of conserved aromatic residues and the Mid domain providing a binding pocket for the 5' end. The Piwi domain contains an RNAse H motif that was cryptic in the primary sequence but easily recognizable in the tertiary structure. Loading of a highly complementary target into an Ago brings the scissile phosphate, opposite nucleotides 10 and 11 of the small RNA guide, into the enzyme active site, allowing cleavage of the RNA to leave 5' P and 3' OH termini (Elbashir, S. et al. *Genes Dev* 15, 188-200 (2001), Elbashir, S. M., et al. *EMBO J* 20, 6877-88 (2001), Yuan, Y. R. et al. *Mol Cell* 19, 405-19 (2005). Martinez, J. & Tuschl, T. *Genes Dev* 18, 975-80 (2004), Schwarz, D. S., et al. *Curr Biol* 14, 787-91 (2004)).

Ago proteins can be divided into three clades. The Piwi Glade is animal specific, and forms part of an elegant innate immune system that controls the activity of mobile genetic elements (Malone, C. D. & Hannon, G. J. *Cell* 136, 656-68 (2009)). The Wago Glade is specific to worms and acts in a variety of different biological processes (Yigit, E. et at. *Cell* 127, 747-57 (2006)). The Ago Glade is defined by similarity to Arabidopsis Ago1 (Bohmert, K. et al. *EMBO J* 17, 170-80 (1998)). Ago-Glade proteins are found in both plants and animals where one unifying thread is their role in gene regulation. In plants, some Ago family members bind to microRNAs and are directed thereby to recognize and cleave complementary target mRNAs (Baumberger, N. & Baulcombe, D. C. *Proc Natl Acad Sci USA* 102, 11928-33 (2005), Qi, Y., Denli, A. M. & Harmon, G. *J. Mol Cell* 19, 421-8 (2005)).

Animal microRNAs function differently from their plant counterparts, with nearly all microRNA-target interactions providing insufficient complementarity to properly orient the scissile phosphate for cleavage. Here, target recognition relies mainly on a "seed" sequence corresponding to miRNA nucleotides (Joshua-Tor, L. *Cold Spring Harb Symp Quant Biol* 71, 67-72 (2006), Malone, C. D. & Hannon, G. J. *Cell* 136, 656-68 (2009)). While pairing of the target to other parts of the miRNA can contribute to recognition, seed pairing appears to be the dominant factor in determining regulation (Yekta, S. et al. *Science* 304, 594-6 (2004)). A very few extensive microRNA-target interactions can lead to target cleavage in mammals (Davis, E. et al. *Curr Dial* 15, 743-9 (2005), Harfe, B. D. et al., *Proc Natl Acad Sci USA* 102, 10898-903 (2005)). However, none of these has yet been shown to be critical for target regulation (Sekita, Y. et al. *Nat Genet* 40, 243-8 (2008), Hornstein, E. et al. *Nature* 438, 671-4 (2005), Tolia, N. H. & Joshua-Tor, L. *Nat Chem Biol* 3, 36-43 (2007)).

Despite the fact that animal microRNAs regulate targets without Ago-mediated cleavage, the Argonaute catalytic center is deeply conserved. This consists of a catalytic DDH triad that serves as a metal coordinating site (Liu, J. et al. *Science* 305, 1437-41 (2004)). Of the four Ago-clade proteins in mammals, only Ago2 has retained both the DDH motif and demonstrable endonuclease activity (Rivas, F. V. et al. *Nat Struct Mol Biol* 12, 340-9 (2005), Song, J. et al. *Science* 305, 1434-7 (2004), Azuma-Mukai, A. et al. *Proc Natl Acad Sci USA* 105, 7964-9 (2008)). Ago1, Ago3, and Ago4 are linked within a single ~190 kb locus and have lost catalytic competence. An analysis of Ago2 mutant cells has indicated that proteins encoded by the Ago 1/3/4 locus can support miRNA-mediated silencing (Rivas, F. V. et al. *Nat Struct Mol Biol* 12, 340-9 (2005)). This leaves us without a clear explanation for the maintenance of a catalytically competent Ago family member, since miRNAs are the exclusive partners of these proteins in almost all cell types (Babiarz, J. E., Ruby, J. G., Wang, Y., Bartel, D. P. & Blelloch, R., *Genes Dev* 22, 2773-85 (2008); Ender, C. et al. *Mol Cell* 32, 519-28 (2008) Tam, O. C. et al. *Nature.* 453:534-538 (2008); Kaneda, M. et al., *Epigenetics Chromatin,* 2:9 (2009)).

2. SUMMARY OF THE INVENTION

Each embodiment disclosed herein is contemplated as being applicable to each of the other disclosed embodiments.

Thus, all combinations of the various elements described herein are within the scope of the invention.

Provided is an improved design of shRNA based on structural mimics of miR-451 precursors. These miR-451 shRNA mimics are channeled through a novel small RNA biogenesis pathway, require AGO2 catalysis and are processed by Drosha but are independent of DICER processing. This miRNA pathway feeds active elements only into Ago2 because of its unique catalytic activity. These data demonstrate that this newly identified small RNA biogenesis pathway can be exploited in vivo to produce active molecules.

Use of miR-451 shRNA mimics provides a distinct advantage over conventional shRNAs in that only one active strand is generated, thereby eliminating off-target effects that could result from incorporation of the sense strand of the duplex into an active RISC. The design of a miR-451 shRNA mimic is very simple and does not require use of sequences from the miR-451 precursor molecule as it is only a structural mimic. However, parts of the primary miRNA-451 sequence, or of the primary sequence of another miRNA may be used in some embodiments, e.g., in aspects of the invention relating to primary shRNA mimics. In some aspects of the invention, primary miR-451 mimics are processed by the drosha step of miR-451 processing while bypassing the canonical pathway, e.g. in certain shRNAs of the invention that are loaded into Ago2 directly.

In one aspect, the invention provides for design and use of miR-451 shRNA mimics based on existing siRNA molecules. In another aspect, the invention provides for design and use of miR-451 shRNA mimics based on any 21-23 nt sequence in the coding region of a target gene. In another aspect, the invention provides for design and use of miR-451 shRNA mimics based on any 21-23 nt sequence in the non-coding region of a target gene. In particular, the miR-451 shRNA mimic comprises a sequence that is fully complementary to a 21 to 23 nucleotide long sequence in the target gene, or to the 21 to 23 nucleotide target sequence of the siRNA. In another aspect of the invention, the miR-451 shRNA mimic comprises a sequence that is fully complementary to a 15 nucleotide long sequence in the target gene, or to a 15 nucleotide target sequence of the siRNA, wherein at least three nucleotides of the guide strand of the miR-451 mimic are in the loop of the shRNA hairpin. In another aspect of the invention, the miR-451 shRNA mimic comprises a sequence that is fully complementary to a 16 nucleotide long sequence in the target gene, or to a 16 nucleotide target sequence of the siRNA, wherein at least three nucleotides of the guide strand of the miR-451 mimic are in the loop of the shRNA hairpin. In designing the miR-451 shRNA mimic, this fully complementary sequence is positioned within the shRNA, such that Ago2 processing of the shRNA and further trimming within the RISC complex generates an active silencing molecule comprising said fully complementary sequence.

In some embodiments, the shRNA of the invention is a synthetic shRNA.

In a non-limiting example, design of a miR-451 mimic shRNA targeting p53 is depicted in (FIG. 3). The resulting ~40 nt shRNA has a short stem and a tight loop and cannot be processed by DICER. Instead, it is cleaved by AGO2 and then further trimmed to generate the active strands targeting p53 mRNA. In another non-limiting example described herein below in Example 6, p53 may be knocked down using the primary sequence backbone of miR-451 by grafting a p53-targeting shRNA sequence into the primary sequence of miR-451.

In one aspect of the invention, an shRNA is provided comprising a first sequence of 19, 20 or 21 nucleotides fully complementary to a sequence in a target gene, having a sequence other than the mature sequence of miR-451, and a second sequence directly following the first sequence, wherein the second sequence is fully complementary to the sequence of the first 15 or 16 nucleotides counted from the 5' end of the first sequence.

In one aspect of the invention, an shRNA is provided comprising a first sequence of 21, 22 or 23 nucleotides complementary to a sequence in a target gene, and a second sequence directly following the first sequence, wherein the second sequence is fully complementary to the sequence of the first 17 nucleotides counted from the 5' end of the first sequence.

In one aspect of the invention, an shRNA is provided comprising a first sequence of 21, 22 or 23 nucleotides fully complementary to a sequence in the coding region of a target gene, and a second sequence directly following the first sequence, wherein the second sequence is complementary to the sequence of the first 17 nucleotides counted from the 5' end of the first sequence.

In one aspect of the invention, an shRNA is provided comprising a first sequence of 21, 22 or 23 nucleotides complementary to a sequence in a target gene, having a sequence other than the mature sequence of miR-451, and a second sequence directly following the first sequence, wherein the second sequence is complementary to the sequence of the first 17 nucleotides counted from the 5' end of the first sequence.

In one aspect of the invention, an shRNA is provided having the structure

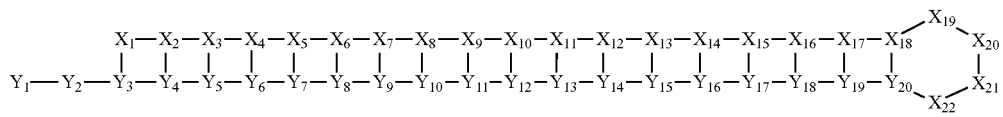

wherein $X_2$ to $X_{22}$ are nucleotides complementary to a sequence in a target gene, and are in a sequence other than the mature sequence of miR451; $Y_4$ to $Y_{20}$ are nucleotides complementary to $X_2$ to $X_{18}$; and $X_1$, $Y_1$, $Y_2$, and $Y_3$, are nucleotides that may be present or absent, wherein $X_1$ and $Y_3$, when present, may be complementary or not complementary.

In one aspect of the invention, an shRNA is provided comprising a first sequence of 21, 22 or 23 nucleotides fully complementary to a sequence in the coding region of a target gene, and a second sequence directly following the first sequence, wherein the second sequence is fully complementary to the sequence of the first 17 or 18 nucleotides counted from the 5' end of the first sequence.

In various embodiments of the instant shRNA, the last 3 nucleotides, or alternatively the last 4 nucleotides, of the first sequence form a loop region in the short hairpin molecule.

In various embodiments of the instant shRNA, the shRNA has a 1 nucleotide overhang at its 3' end, or alternatively a 2, 3 or more than 3 nucleotide overhang at its 3' end.

In various embodiments of the instant shRNA, the shRNA has a 1 nucleotide overhang at its 5' end, or alternatively a 2, 3 or more than 3 nucleotide overhang at its 5' end.

In an embodiment of the instant shRNA, the shRNA has no 3' or 5' overhang.

In an embodiment of the instant shRNA, the shRNA consists of a first sequence of 21, 22 or 23 nucleotides fully complementary to a sequence in the coding region of a target gene, and a second sequence directly following the first sequence, wherein the second sequence is fully complementary to the sequence of the first 17 or 18 nucleotides counted from the 5' end of the first sequence.

In one aspect of the invention, an shRNA is provided comprising a first sequence of 21, 22 or 23 nucleotides fully complementary to a sequence in an intron or other non-coding region of a target gene, and a second sequence directly following the first sequence, wherein the second sequence is fully complementary to the sequence of the first 17 or 18 nucleotides counted from the 5' end of the first sequence.

In some embodiments of the invention, an shRNA comprises a first sequence of 21, 22, or 23 nucleotides fully complementary to a sequence in a non-coding target gene.

In some embodiments of the invention, an shRNA comprises a first sequence of 21, 22, or 23 nucleotides fully complementary to a sequence in a target long non-coding RNA.

In various embodiments of the instant shRNA, the last 3 nucleotides, or alternatively the last 4 nucleotides, of the first sequence form a loop region in the short hairpin molecule.

In various embodiments of the instant shRNA, the shRNA has a 1 nucleotide overhang at its 3' end, or alternatively a 2, 3 or more than 3 nucleotide overhang at its 3' end.

In various embodiments of the instant shRNA, the shRNA has a 1 nucleotide overhang at its 5' end, or alternatively a 2, 3 or more than 3 nucleotide overhang at its 5' end.

In an embodiment of the instant shRNA, the shRNA has no 3' or 5' overhang.

In an embodiment of the instant shRNA, the shRNA consists of a first sequence of 21, 22 or 23 nucleotides fully complementary to a sequence in the coding region of a target gene, and a second sequence directly following the first sequence, wherein the second sequence is fully complementary to the sequence of the first 17 or 18 nucleotides counted from the 5' end of the first sequence.

Other aspects of the invention include an expression vector comprising a sequence encoding an shRNA as described herein, operably linked to an RNA polymerase promoter, and a library of such expression vectors. The expression vector or library of expression vectors can be introduced into a mammalian cell in vitro or in vivo in a method of attenuating target gene expression. The shRNA is expressed in an amount sufficient to attenuate target gene expression in a sequence specific manner. In a preferred embodiment, the shRNA is stably expressed in the mammalian cell.

In one aspect of the invention a method is provided for attenuating expression of a target gene in a mammalian cell, the method comprising introducing into the mammalian cell an expression vector comprising a sequence encoding a short hairpin RNA molecule (shRNA) operably linked to an RNA polymerase promoter, the shRNA comprising:

(i) a first sequence of 21, 22 or 23 nucleotides fully complementary to a sequence in the coding region of the target gene, (ii) a second sequence directly following the first sequence, wherein the second sequence is fully complementary to the sequence of the first 17 or 18 nucleotides counted from the 5' end of the first sequence, wherein the shRNA molecule is expressed in the mammalian cell in an amount sufficient to attenuate expression of the target gene in a sequence specific manner, whereby expression of the target gene is inhibited.

In certain embodiments, the instant expression vector comprises a sequence encoding the shRNA according operably linked to an RNA polymerase promoter. In certain embodiments, the invention provides for use of a library of expression vectors, wherein each expression vector comprises a sequence encoding the shRNA operably linked to an RNA polymerase promoter.

In another method of attenuating target gene expression, the shRNA of the invention is introduced into a mammalian cell in an amount sufficient to attenuate target gene expression in a sequence specific manner. The shRNA of the invention can be introduced into the cell directly, or can be complexed with cationic lipids, packaged within liposomes, or otherwise delivered to the cell. In certain embodiments the shRNA can be a synthetic shRNA, including shRNAs incorporating modified nucleotides, such as those with chemical modifications to the 2'-OH group in the ribose sugar backbone, such as 2'-O-methyl (2'OMe), 2'-fluoro (2'F) substitutions, and those containing 2'OMe, or 2'F, or 2'-deoxy, or "locked nucleic acid" (LNA) modifications. In some embodiments, an shRNA of the invention contains modified nucleotides that increase the stability or half-life of the shRNA molecule in vivo and/or in vitro. Alternatively, the shRNA can comprise one or more aptamers, which interact(s) with a target of interest to form an aptamer:target complex. The aptamer can be at the 5' or the 3' end of the shRNA. Aptamers can be developed through the SELEX screening process and chemically synthesized. An aptamer is generally chosen to preferentially bind to a target. Suitable targets include small organic molecules, polynucleotides, polypeptides, and proteins. Proteins can be cell surface proteins, extracellular proteins, membrane proteins, or serum proteins, such as albumin. Such target molecules may be internalized by a cell, thus effecting cellular uptake of the shRNA. Other potential targets include organelles, viruses, and cells.

Also included in the invention is an isolated mammalian cell comprising the shRNAs described herein. In a preferred embodiment, the mammalian cell is a human cell. Another aspect of the invention provides a non-human mammal comprising the cell described above. In certain embodiments, the non-human mammal may be a chimeric mammal, some of whose somatic or germ cells comprising the shRNAs described herein. Alternatively, the non-human mammal may be a transgenic mammal, all of whose somatic or germ cells comprise the shRNAs described herein. Thus, transgenic mammals whose genomes comprise a sequence encoding the shRNAs of the invention are also provided. In one embodiment, the transgenic mammal is a mouse.

Also included in the invention is an isolated non-mammalian cell comprising the shRNAs described herein. The cells may be those of vertebrate organisms, or non-vertebrate organisms such as insects. The cells may be those of fish (e.g. those of the *Fugu* genus, or the *Danio* genus), frogs (e.g. those of the *Xenopus* genus), round worms (e.g. those of the *Caenorhabdis* genus), flies (such as the *Drosophila* genus), or others. Another aspect of the invention provides a non-human animal comprising the cell described above. In certain embodiments, the non-human animal may be a chimeric animal, some of whose somatic or germ cells comprising the shRNAs described herein. Alternatively, the non-human animal may be a transgenic animal, all of whose somatic or germ cells comprise the shRNAs described herein. Thus, transgenic animals whose genomes comprise a sequence encoding the shRNAs of the invention are also provided.

Another aspect of the invention provides for design of miRNAs based on structural mimics of miR-451 precursors. In certain embodiments, such structural miRNA mimics of miR-451, or an expression vector or library of expression vectors encoding such structural mimics can be introduced into different genetic backgrounds of mammalian cells, in particular in cells deficient of the canonical pathway enzymes, such as dicer, to screen for and identify such miRNAs capable of rescuing the null phenotype and the functional roles of such miRNAs in contributing to the phenotype.

In one aspect of the invention, a non-naturally occurring miRNA is provided comprising a first sequence of 21, 22 or 23 nucleotides corresponding to the entire mature sequence, or a portion of that sequence, of a mammalian miRNA other than miR-451, and a second sequence directly following the first sequence, wherein the second sequence is fully complementary to the sequence of the first 17 or 18 nucleotides counted from the 5' end of the first sequence. The skilled practitioner will appreciate that the mature sequence of a mammalian miRNA alternatively may be identified as the sequence of the guide strand, or guide sequence for that miRNA.

In various embodiments of the instant non-naturally occurring miRNA, the last 3 nucleotides, or alternatively the last 4 nucleotides, of the first sequence form a loop region in the short hairpin molecule.

In various embodiments of the instant non-naturally occurring miRNA, the non-naturally occurring miRNA has a 1 nucleotide overhang at its 3' end, or alternatively a 2, 3 or more than 3 nucleotide overhang at its 3' end.

In various embodiments of the instant non-naturally occurring miRNA, the non-naturally occurring miRNA has a 1 nucleotide overhang at its 5' end, or alternatively a 2, 3 or more than 3 nucleotide overhang at its 5' end.

In an embodiment of the instant non-naturally occurring miRNA, the non-naturally occurring miRNA has no 3' or 5' overhang.

An aspect of the invention provides a composition comprising an shRNA comprising a first sequence of 21, 22 or 23 nucleotides fully complementary to a sequence in the coding region of a target gene, and a second sequence directly following the first sequence, wherein the second sequence is fully complementary to the sequence of the first 17 or 18 nucleotides counted from the 5' end of the first sequence.

An aspect of the invention provides a pharmaceutical composition comprising an shRNA comprising a first sequence of 21, 22 or 23 nucleotides fully complementary to a sequence in the coding region of a target gene, and a second sequence directly following the first sequence, wherein the second sequence is fully complementary to the sequence of the first 17 or 18 nucleotides counted from the 5' end of the first sequence.

An aspect of the invention provides an shRNA comprising a first sequence of 21, 22 or 23 nucleotides fully complementary to a sequence in the coding region of a target gene, and a second sequence directly following the first sequence, wherein the second sequence is fully complementary to the sequence of the first 17 or 18 nucleotides counted from the 5' end of the first sequence for the manufacture of a medicament.

3. BRIEF DESCRIPTION OF THE DRAWINGS

FIGS. 1A-D show use of miR-451 shRNA mimics for RNAi in mammalian cells. Schematic depictions of the pre-let-7c-miR-451 mimic hairpin (SEQ ID NO: 1) compared to the native pre-let-7c (SEQ ID NO: 2). Guide strand in red and passenger strand in blue. (FIG. 1A) Overlapping GFP histograms reporting the activity of let-7c molecules using GFP let-7c sensor ES cells. Cells were co-transfected with PE-siRNA control. 105 PE positive cells were gated and analyzed for GFP expression. (FIG. 1B) Dual luciferase assay reporting mature let-7 activity. Top: Schematic of let-7 MSCV-luciferase reporter construct containing two perfectly matching let-7c sites at the 3'UTR. Bottom: Histogram showing luminescence values of luciferase/renilla ratios. Data are the mean of three technical replicates±SD. (FIG. 1C) Top panel: schematic of the p53 hairpin design in the mir-30 backbone (SEQ ID NO: 3) or mimicking the miR-451 fold (SEQ ID NO: 4). Bottom panel: Western blot analysis showing p53 knockdown in ES cells upon transfection of p53 hairpins and induction of p53 with adriamycin. (FIG. 1D)

FIGS. 2A-B show steps in the biogenesis of miR-451shRNA. Model of miR-451 biogenesis using an artificial MSCV expression plasmid. The primary transcript, driven by the LTR promoter, is processed by drosha to release the 40 nt pre-miR-451 (SEQ ID NO: 5) that is processed by Ago2 to generate the active RISC complex. (FIG. 2A) IP-northerns showing processing of the mature miR-451 only in the Ago2 immunoprecipitates. Ago1 complexes could load pre-miR-451 but were unable to process it to its mature form. (FIG. 2B)

FIGS. 3A-B show a schematic example for generating a miR-451 mimic molecule. Here p53-shRNA-1224 is shown as an example targeting the following site in the p53 message: UCCACUACAAGUACAUGUGUAA (SEQ ID NO: 6). FIG. 3A depicts the canonical miRNA processing pathway using the mir-30 backbone of the p53 hairpin (SEQ ID NO: 7). The mir-30 loop sequence in green. The strands are color coded: antisense strand in red and sense strand corresponding to the target site in blue. DICER RNAseIII cut sites are depicted using arrows. FIG. 3B shows the generation of the p53-1224 shRNA mimicking miR-451 structure that can be channeled through the Ago2 mediated miRNA biogenesis pathway. The antisense strand (red) spanning the stem is designed to extend into the loop. The passenger arm is highlighted in blue. Ago2 catalysis of the predicted phosphodiester bond is shown using scissors. This pathway generates only Ago2 active RISC.

FIGS. 4A-C show mature miR-451 expression depends on Ago2 catalysis. Scatter plot of miRNA reads in wild-type versus mutant fetal liver. (FIG. 4A). Quantitative RT-PCR of primary transcript levels of mir-144 (SEQ ID NO: 8) and miR-451 (SEQ ID NO: 9) in wt and mutant liver samples. Data are the mean of three biological replicates+/−SD*t-test with equal variance p>0.05. (FIG. 4B). The unique structure of the miR-451 hairpin compared to mir-144 with the mirbase annotation of mature miR-451 and mir-144 mapped to the predicted secondary hairpin structure shown. Guide strand in red and passenger strand in blue. (FIG. 4C).

FIGS. 5A-5F show the non-canonical biogenesis of miR-451. Effect on mature miRNA levels of Drosha conditional ablation in Drosha flox/flox Cre-ER MEFs. (FIG. 5A). In-vitro processing of miR-451 and mir-144 primary transcripts by Drosha immunoprecipitates. pre-miR144 and pre-miR451 are indicated with their corresponding expected sizes. Additional fragments released by possible Drosha processing of the 5' miR-451 flank are indicated with asterisks. Flanks are indicated with arrowheads. (FIG. 5B). Northern blots for confirmation of in-vitro Drosha processing assays. (FIG. 5C). Effect on mature miRNA levels of Dicer conditional ablation in Dicer flox/flox Cre-ER ES cells. (FIG. 5D) Effects on mature miRNA levels in Dicer null stable ES cells. (FIG. 5E). Mature miR-451 expression in dicer-null stable ES cells. U6 is used as a loading control. (FIG. 5F).

FIGS. 6A-6D show Ago2 catalysis is required for miR-451 biogenesis. Left panels: Northern blot on total RNA from wt and mutant livers probing for miR-451 guide strand and passenger arms of the hairpin (indicated). Let-7 is used as a loading control. Right panels: Northern blots of Ago2 and IgG control immunoprecipitates from wt and mutant liver extracts with the indicated probes. (FIG. 6A). miRNA read length distribution for the indicated miRNA from deep sequencing of WT and mutant livers. (FIG. 6B). Prediction of a miR-451 Ago2 cleavage site. top: miR-451 3' end heterogeneity. Bottom: predicted cleavage site at the 30th phosphodiester bond of pre-miR-451. (FIG. 6C). Left gel: in-vitro cleavage assay of pre-miR-451 by an Ago2 immunoprecipitate. Right gel: confirmation of the 3' end character of the Ago2 cleavage product using beta elimination and 3' end ligation reactions. (FIG. 6D).

FIG. 7 shows expression of miR-451 shRNA structural mimics. A mir-144-451 fragment cloned in the MluI/BglII site of vector and encompassing the mir-144-455 cluster sequence is amplified out of the human genome. From the amplified fragment, a miR-451 cassette is generated by subcloning a fragment of the mir-144-451 cluster sequence comprising 5' and 3' miR-451 flanking sequences, engineering restriction sites on each of the 5' and 3' ends of that fragment, and subcloning the resulting cassette into an MSCV expression plasmid backbone. An MSCV expression construct encoding a miR-451 shRNA mimic targeted against p53 mRNA is generated by replacing the native miR-451 precursor sequence (shaded portion; AAACCGTTACCATTACT-GAGTTTAGTAATGGTAATGGTTCT) (SEQ ID NO: 11) with a sequence encoding the mir-451 shRNA mimic FIG. 8 shows that MicroRNA-451 based shRNA precursors (drosha products) are functional in mouse embryonic stem (ES) cells and manifest a different dose response compared to miR-30 based shRNAs precursor mimics.

FIG. 9 shows that primary MicroRNA-451 based shRNA is functional, allowing the stable expression of the miR-451 mimics using a miR-451 backbone.

Figure 11A:
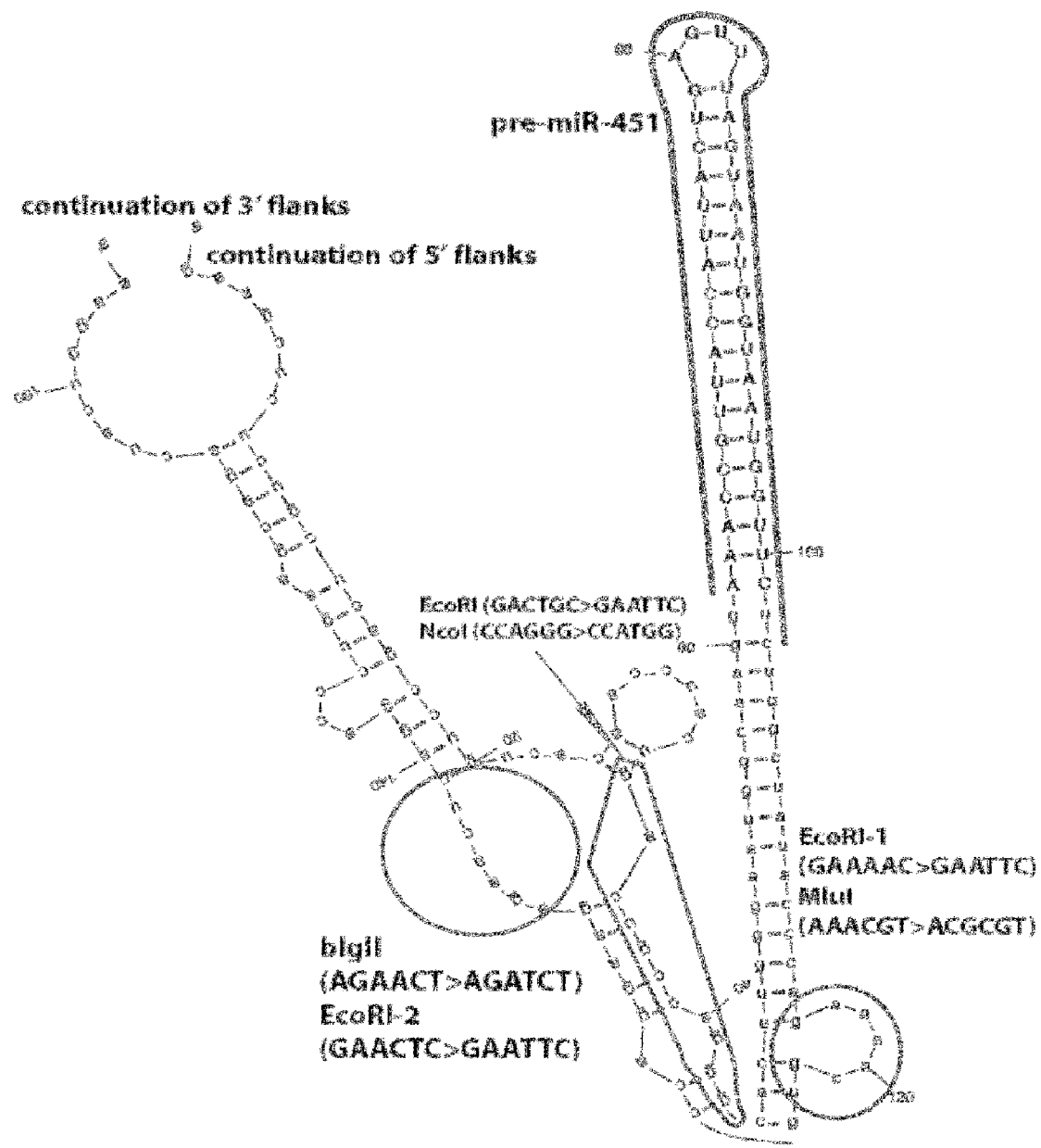
Figure 11B:
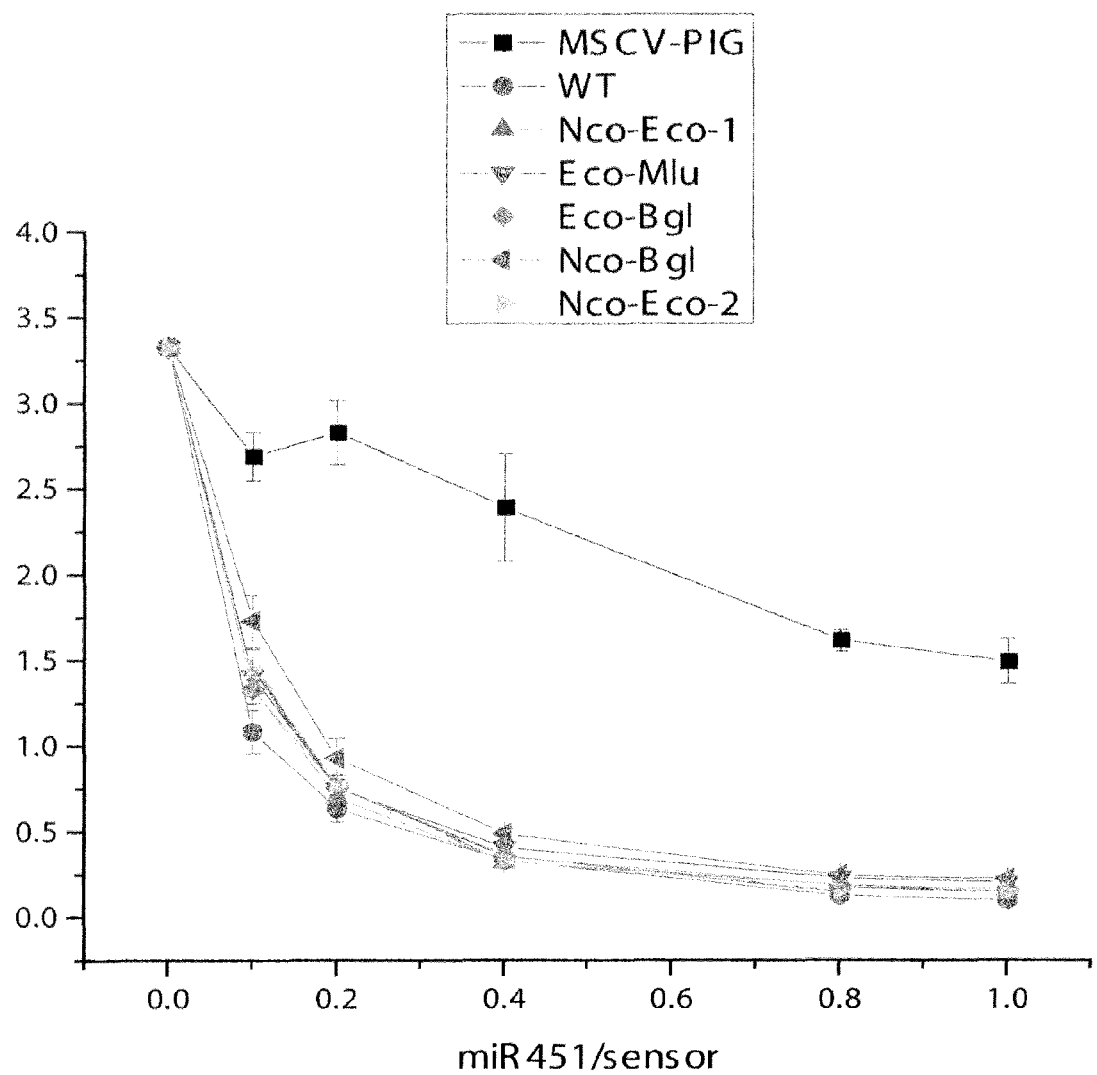

FIG. 11 shows the generation of a graftable primary miR-451 longer backbone through the introduction of Restriction sites into the endogenous miR-451 sequence for cloning purposes. (FIG. 11A), Design of restriction sites in the miR-144-451 cloned backbone into MSCV retroviral expression vector. Note that restriction sites are located outside of the predicted Drosha complex recognition region. Flanking sequences are in lower case with the extent of the drosha processed precursor being covered by the gray bar. In the present case, the drosha processed product can include now 3' flanking nucleotides. (FIG. 11B) miR-451 luciferase sensor assay analysis showing no interruption of mature microRNA silencing efficiency. Titrations of MiR-45'-firefly luciferase sensor construct and endogenous primary microRNA constructs harboring wild-type or mutant miR-451 with the corresponding restriction sites from (FIG. 11A) co-transfected with renilla constructs. Luciferase level was measured by dual luciferase reporter assay. MSCV-PIG is used as a negative control.

Figure 12:
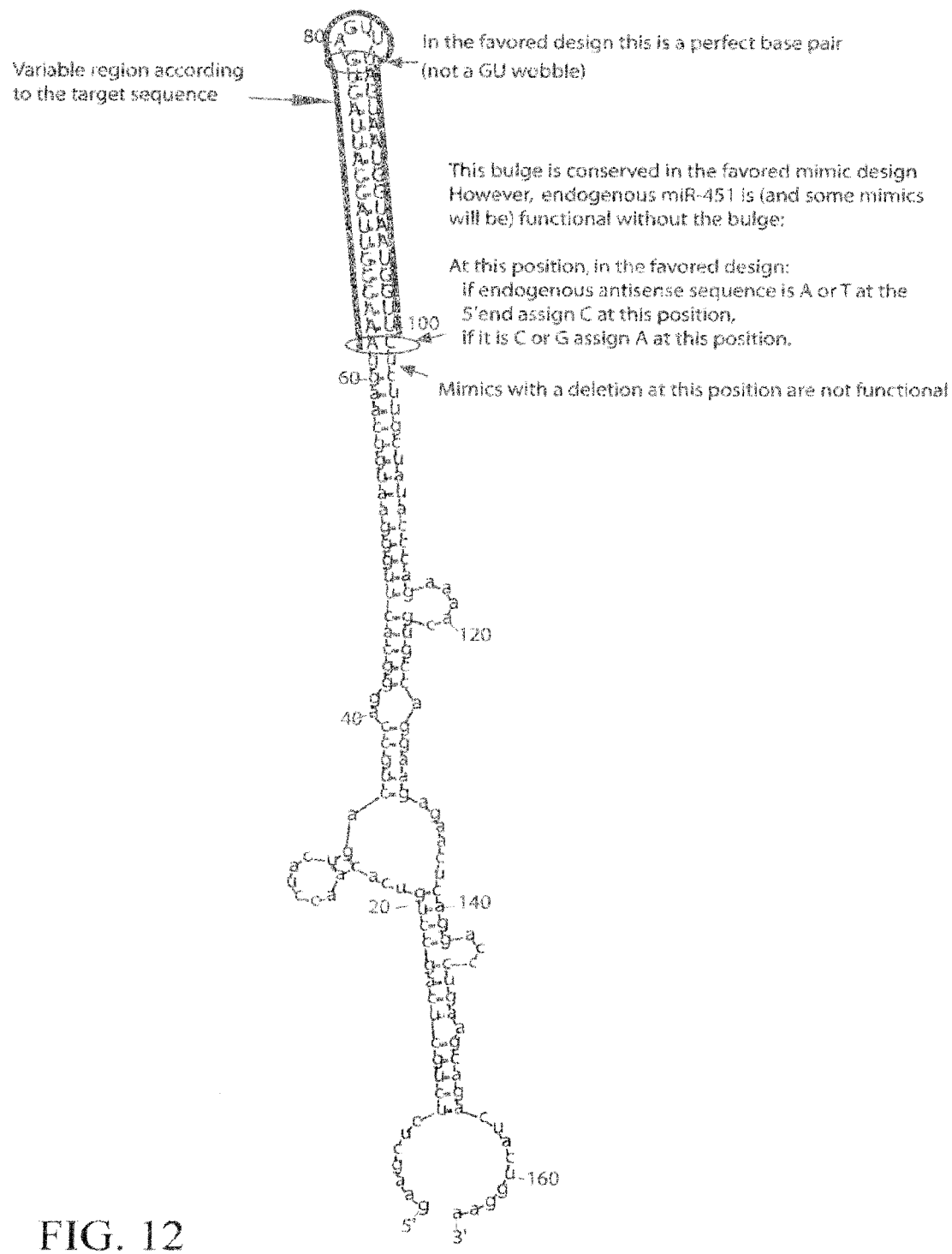

FIG. 12 shows an example of miR-451 mimic design. Predicted secondary structure of the minimal endogenous primary miR-451 sequence used for stable expression. The mimics are grafted within the shRNA variable region highlighted in green according to the target sequence in the gene. Note that the GU wobble is converted to a perfect base pair in the mimics, the bulge in the basal stem is conserved and we have shown experimentally that the deletion of the T at position 41 makes non-functional mimics, suggesting a structural requirement for drosha processing.

Figure 13A:
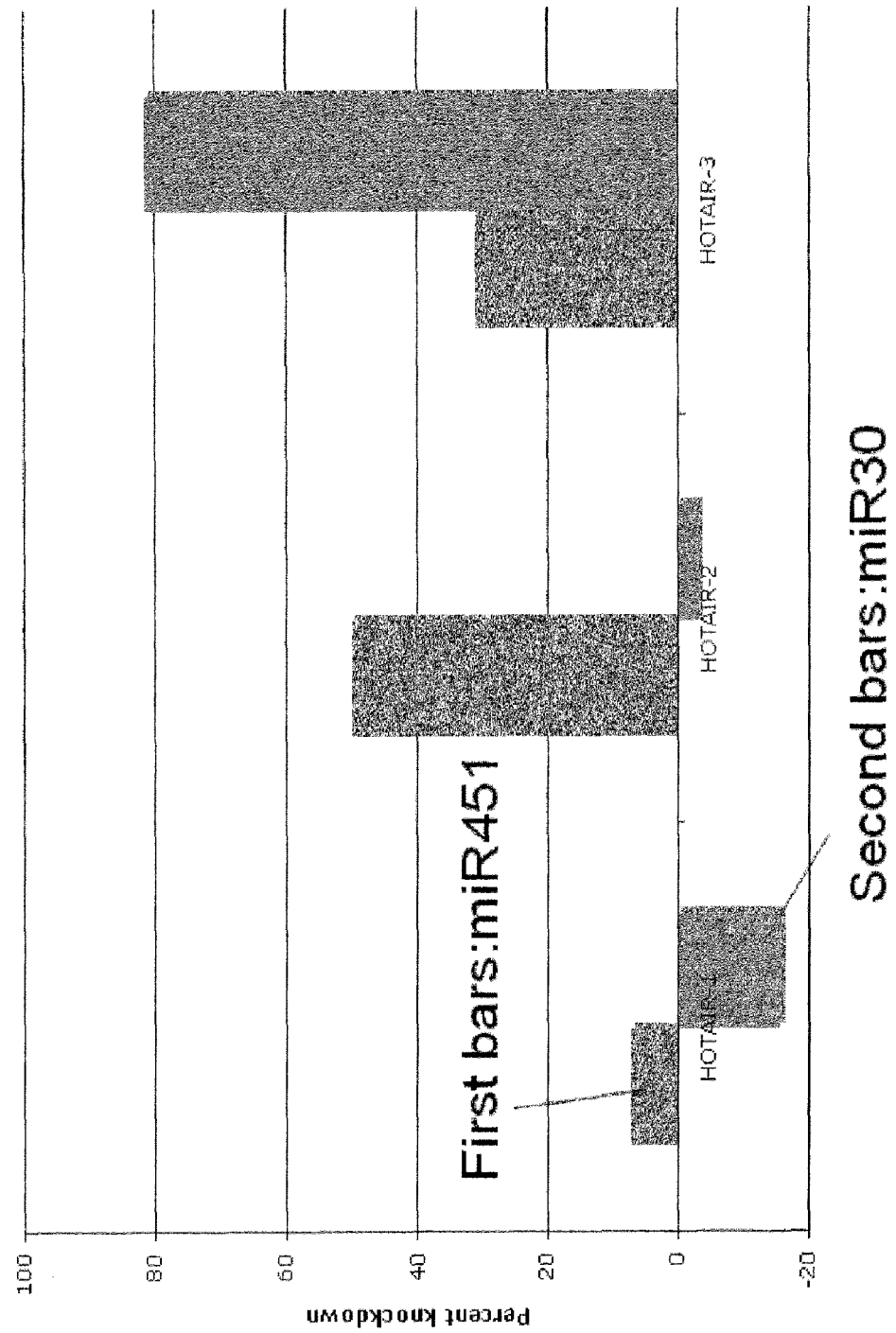
Figure 13B:
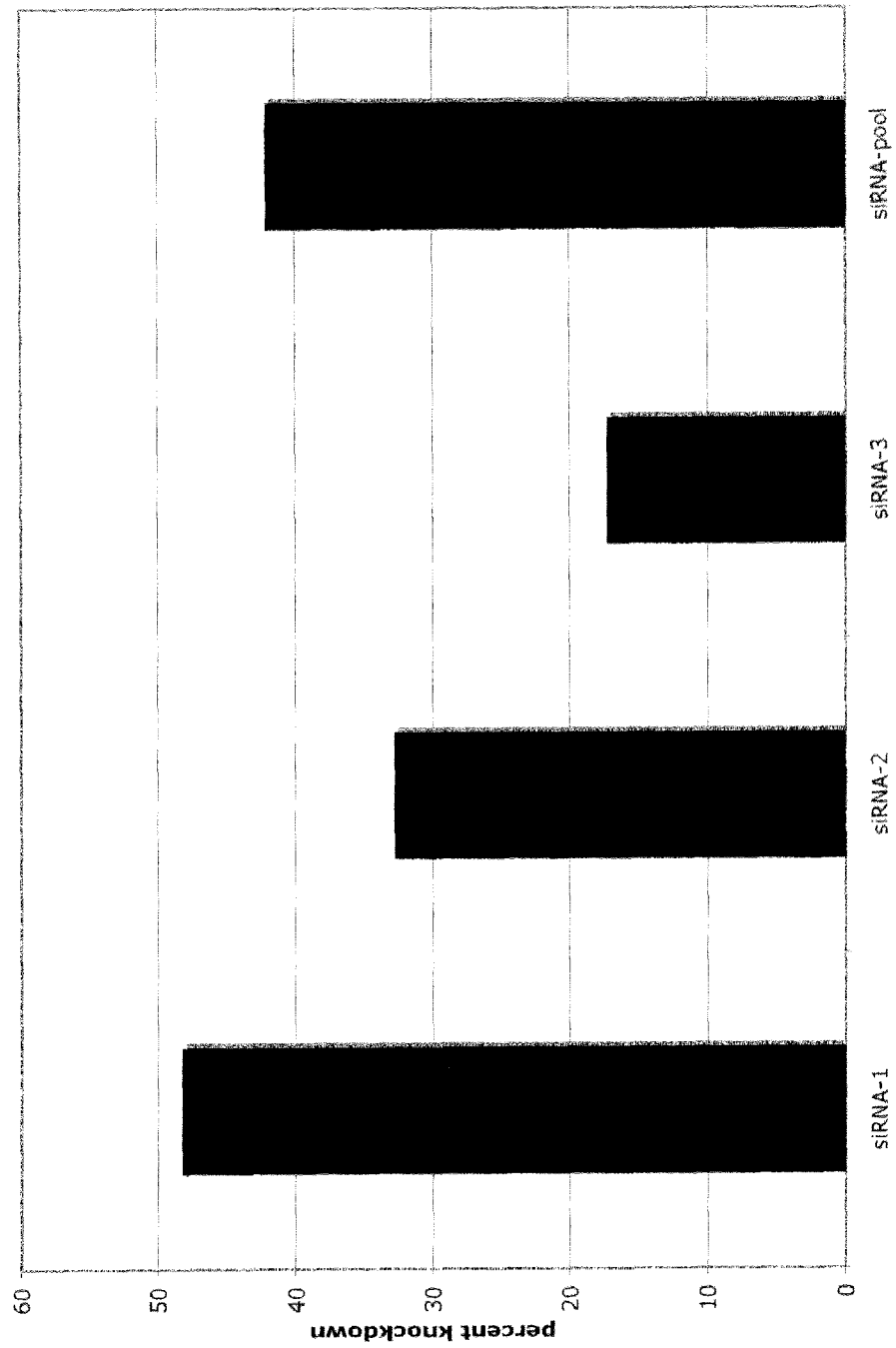

FIG. 13 shows HOTAIR shRNA knockdown in stable MCG7 lines expressing miR-451 mimic hairpins or miR30 mimic hairpins (FIG. 13A). Experiments were also conducted using siRNA HOTAIR knockdown in the MCF-7 cell line (FIG. 13B).

4. DETAILED DESCRIPTION OF THE INVENTION

4.1 General Definitions

As used herein, the term "sequence" may mean either a strand or part of a strand of nucleotides, or the order of nucleotides within a strand a or part of a strand, depending on the appropriate context in which the term is used. Unless specified otherwise in context, the order of nucleotides is recited from the 5' to the 3' direction of a strand.

A "coding sequence" or a sequence "encoding" a particular molecule is a nucleic acid that is transcribed (in the case of DNA) or translated (in the case of mRNA) into an inhibitory RNA (e.g., an shRNA or an antisense) or polypeptide, in vitro or in vivo, when operably linked to an appropriate regulatory sequence. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the coding sequence.

As used herein, a sequence "directly following" a first sequence, in describing an shRNA, means a sequence extending from, e.g. the 3' end of, the first sequence without any nucleotides intervening therebetween.

As used herein, the term "fully complementary" with regard to a sequence refers to a complement of the sequence by Watson-Crick base pairing, whereby guanine (G) pairs with cytosine (C), and adenine (A) pairs with either uracil (U) or thymine (T). A sequence may be fully complementary to the entire length of another sequence, or it may be fully complementary to a specified portion or length of another sequence. One of skill in the art will recognize that U may be present in RNA, and that T may be present in DNA. Therefore, an A within either of a RNA or DNA sequence may pair with a U in a RNA sequence or T in a DNA sequence.

As used herein, the term "wobble base pairing" with regard to two complementary nucleic acid sequences refers to the base pairing of G to uracil U rather than C, when one or both of the nucleic acid strands contains the ribonucleobase U.

As used herein, the term "substantially fully complementary" with regard to a sequence refers to the reverse complement of the sequence allowing for both Watson-Crick base pairing and wobble base pairing, whereby G pairs with either C or U, and A pairs with either U or T. A sequence may be substantially complementary to the entire length of another sequence, or it may be substantially complementary to a specified portion or length of another sequence. One of skill in the art will recognize that the U may be present in RNA, and that T may be present in DNA. Therefore, a U within an RNA sequence may pair with A or G in either an RNA sequence or a DNA sequence, while an A within either of a RNA or DNA sequence may pair with a U in a RNA sequence or T in a DNA sequence.

As used herein, the term "canonical" with regard to RNAi means, requiring cleavage by DICER for the maturation of an shRNA molecule. Therefore, a "canonical shRNA" is an shRNA that requires cleavage by DICER before becoming a mature shRNA, and a "canonical pathway" as it relates to shRNA-mediated RNAi is a pathway involving the cleavage of a non-mature shRNA by DICER.

The term "gene" refers to a nucleic acid comprising an open reading frame encoding a polypeptide, including both exon and (optionally) intron sequences. The nucleic acid can also optionally include non-coding sequences such as promoter and/or enhancer sequences.

As used herein, the term "long non-coding RNA" refers to a non-protein coding RNA transcript longer than 200 nucleotides.

The term "mRNA" refers to a nucleic acid transcribed from a gene from which a polypeptide is translated, and may include non-translated regions such as a 5'UTR and/or a 3'UTR. It will be understood that an shRNA of the invention may comprise a nucleotide sequence that is complementary to any sequence of an mRNA molecule, including translated regions, the 5'UTR, the 3'UTR, and sequences that include both a translated region and a portion of either 5'UTR or 3'UTR. An shRNA of the invention may comprise a nucleotide sequence that is complementary to a region of an mRNA molecule spanning the start codon or the stop codon.

"Library" refers to a collection of nucleic acid molecules (circular or linear). In one preferred embodiment, a library (alternatively referred to as a cDNA library) is representative of all expressed genes in a cell, tissue, organ or organism. A library may also comprise random sequences made by de novo synthesis, mutagenesis or other modification or alteration of one or more sequences. A library may be contained in one or more vectors.

"Nucleic acid" refers to polynucleotides such as deoxyribonucleic acid (DNA) and ribonucleic acid (RNA). The term can include single-stranded and double-stranded polynucleotides.

"Operably linked" means that the coding sequence is linked to a regulatory sequence in a manner which allows expression of the coding sequence. Regulatory sequences include promoters, enhancers, and other expression control elements that are art-recognized and are selected to direct expression of the coding sequence.

"Recombinant" RNA molecules are those produced by recombinant DNA techniques; i.e., produced from cells transformed by an exogenous DNA construct encoding the desired RNA. "Synthetic" RNA molecules are those prepared by chemical synthesis.

A "subject" or "patient" can be a human or non-human animal.

A "transduced cell" is one that has been genetically modified. Genetic modification can be stable or transient. Methods of transduction (i.e., introducing vectors or constructs into cells) include, but are not limited to, liposome fusion (transposomes), viral infection, and routine nucleic acid transfection methods such as electroporation, calcium phosphate precipitation and microinjection. Successful transduction will have an intended effect in the transduced cell, such as gene expression, gene silencing, enhancing a gene target, or triggering target physiological event.

In one embodiment, "treating" means slowing, stopping or reversing the progression of a disease or disorder. "Treating" can also mean amelioration of symptoms associated with a disease or disorder.

"Vector" refers to a vehicle for introducing a nucleic acid into a cell. Vectors include, but are not limited to, plasmids, phagemids, viruses, bacteria, and vehicles derived from viral or bacterial sources. Vectors can also include aptamers, where the aptamer either forms part of, or is conjugated to the RNAi molecule (Dassie et al., Nature Biotechnology 27, 839-846 (2009), Thou and Rossi, Silence, 1:4 (2010), McNamera et al., Nature Biotechnology 24, 1005-1015 (2006)). A "plasmid" is a circular, double-stranded DNA molecule. A useful type of vector for use in the present invention is a viral vector, wherein heterologous DNA sequences are inserted into a viral genome that can be modified to delete one or more viral genes or parts thereof. Certain vectors are capable of autonomous replication in a host cell (e.g., vectors having an origin of replication that functions in the host cell). Other vectors can be stably integrated into the genome of a host cell, and are thereby replicated along with the host genome.

4.2 RNAi Molecules

Interfering RNA or small inhibitory RNA (RNAi) molecules include short interfering RNAs (siRNAs), repeat-associated siRNAs (rasiRNAs), and micro-RNAs (miRNAs) in all stages of processing, including shRNAs, pri-miRNAs, and pre-miRNAs. These molecules have different origins: siRNAs are processed from double-stranded precursors (dsRNAs) with two distinct strands of base-paired RNA; siRNAs that are derived from repetitive sequences in the genome are called rasiRNAs; miRNAs are derived from a single transcript that forms base-paired hairpins. Base pairing of siRNAs and miRNAs can be perfect (i.e., fully complementary) or imperfect, including bulges in the duplex region.

The design of miR-451 shRNA mimics useful in this invention, and in particular, the choice of target sequences for miR-451 shRNA mimics can be based on existing shRNA, siRNA, piwi-interacting RNA (piRNA), micro RNA (miRNA), double-stranded RNA (dsRNA), antisense RNA, or any other RNA species that can be cleaved inside a cell to form interfering RNAs, with compatible modifications described herein. As used herein, shRNAs useful in this invention include, without limitation, modified shRNAs, including shRNAs with enhanced stability in vivo. Modified shRNAs include molecules containing nucleotide analogues, including those molecules having additions, deletions, and/or substitutions in the nucleobase, sugar, or backbone; and molecules that are cross-linked or otherwise chemically modified. The modified nucleotide(s) may be within portions of the shRNA molecule, or throughout it. For instance, the shRNA molecule may be modified, or contain modified nucleic acids in regions at its 5' end, its 3' end, or both, and/or within the guide strand, passenger strand, or both, and/or within nucleotides that overhang the 5' end, the 3' end, or both. (See Crooke, U.S. Pat. Nos. 6,107,094 and 5,898,031; Elmen et al., U.S. Publication Nos. 2008/0249039 and 2007/0191294; Manoharan et al., U.S. Publication No. 2008/0213891; MacLachlan et al., U.S. Publication No. 2007/0135372; and Rana, U.S. Publication No. 2005/0020521; all of which are hereby incorporated by reference.)

As used herein, an "shRNA molecule" includes a conventional stem-loop shRNA, which forms a precursor miRNA (pre-miRNA). "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. When transcribed, a conventional shRNA (i.e., not a miR-451 shRNA mimic) forms a primary miRNA (pri-miRNA) or a structure very similar to a natural pri-miRNA. The pri-miRNA is subsequently processed by Drosha and its cofactors into pre-miRNA. Therefore, the term "shRNA" includes pri-miRNA (shRNA-mir) molecules and pre-miRNA molecules.

A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches.

"RNAi-expressing construct" or "RNAi construct" is a generic term that includes nucleic acid preparations designed to achieve an RNA interference effect. An RNAi-expressing construct comprises an RNAi molecule that can be cleaved in vivo to form an siRNA or a mature shRNA. For example, an RNAi construct is an expression vector capable of giving rise to an siRNA or a mature shRNA in vivo. Non-limiting examples of vectors that may be used in accordance with the present invention are described herein, for example, in section 4.6. Exemplary methods of making and delivering long or short RNAi constructs can be found, for example, in WO01/68836 and WO01/75164.

4.3 Use of RNAi

RNAi is a powerful tool for in vitro and in vivo studies of gene function in mammalian cells and for therapy in both human and veterinary contexts. Inhibition of a target gene is sequence-specific in that gene sequences corresponding to a portion of the RNAi sequence, and the target gene itself, are specifically targeted for genetic inhibition. Three mechanisms of utilizing RNAi in mammalian cells have been described. The first is cytoplasmic delivery of siRNA molecules, which are either chemically synthesized or generated by DICER-digestion of dsRNA. These siRNAs are introduced into cells using standard transfection methods. The siRNAs enter the RISC to silence target mRNA expression.

The second mechanism is nuclear delivery, via viral vectors, of gene expression cassettes expressing a short hairpin RNA (shRNA). The shRNA is modeled on micro interfering RNA (miRNA), an endogenous trigger of the RNAi pathway (Lu et al., 2005, Advances in Genetics 54: 117-142, Fewell et al., 2006, Drug Discovery Today 11: 975-982). Conventional shRNAs, which mimic pre-miRNA, are transcribed by RNA Polymerase II or III as single-stranded molecules that form stem-loop structures. Once produced, they exit the nucleus, are cleaved by DICER, and enter the RISC as siRNAs.

The third mechanism is identical to the second mechanism, except that the shRNA is modeled on primary miRNA (shRNAmir), rather than pre-miRNA transcripts (Fewell et al., 2006). An example is the miR-30 miRNA construct. The use of this transcript produces a more physiological shRNA that reduces toxic effects. The shRNAmir is first cleaved to produce shRNA, and then cleaved again by DICER to produce siRNA. The siRNA is then incorporated into the RISC for target mRNA degradation.

For mRNA degradation, translational repression, or deadenylation, mature miRNAs or siRNAs are loaded into the RNA Induced Silencing Complex (RISC) by the RISC-loading complex (RLC). Subsequently, the guide strand leads the RISC to cognate target mRNAs in a sequence-specific manner and the Slicer component of RISC hydrolyses the phosphodiester bound coupling the target mRNA nucleotides paired to nucleotide 10 and 11 of the RNA guide strand. Slicer forms together with distinct classes of small RNAs the RNAi effector complex, which is the core of RISC. Therefore, the "guide strand" is that portion of the double-stranded RNA that associates with RISC, as opposed to the "passenger strand," which is not associated with RISC.

4.4 Identification of an Alternative miRNA Biogenesis Pathway

Figure 3A:
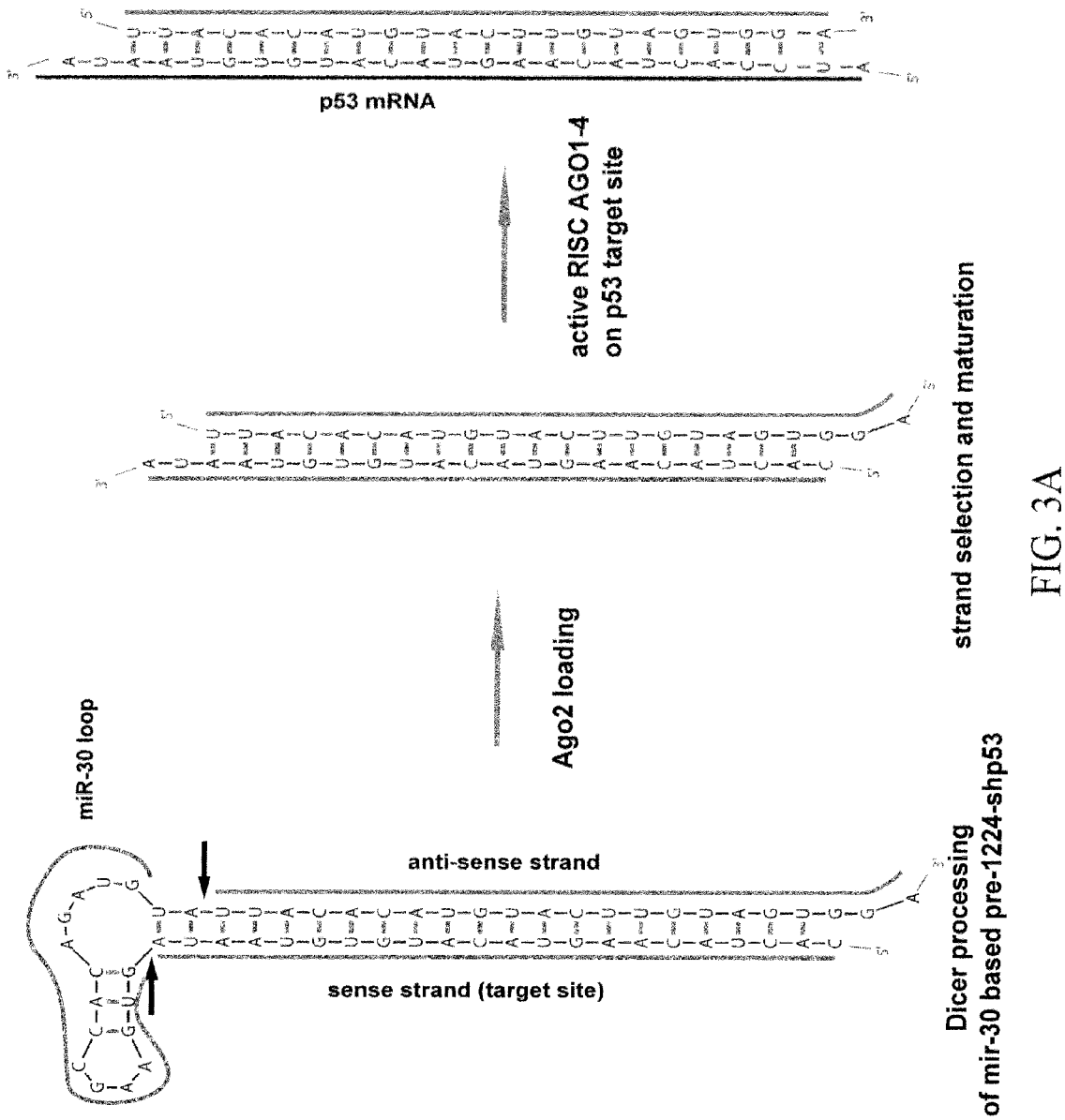
Figure 3B:
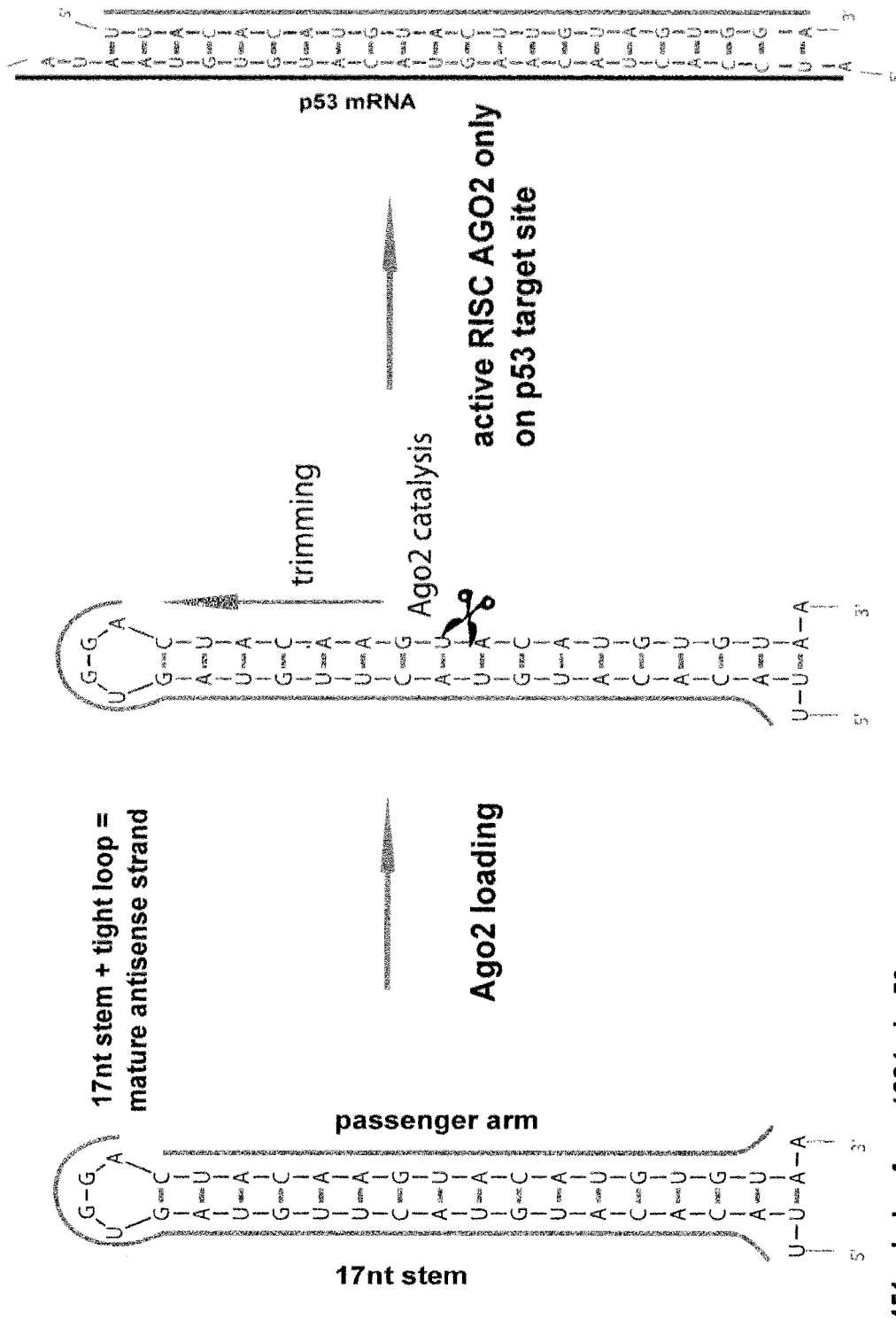

Disclosed herein is that the erythroid specific miRNA miR-451, is channeled through a novel small RNA biogenesis pathway requires AGO2 catalysis and is independent of DICER processing. miR-451 is processed by Drosha, its maturation does not require Dicer. Instead, the pre-miRNA becomes loaded into AGO2 and is cleaved by the AGO catalytic center to generate an intermediate 3'end, which is then further trimmed (Cheloufi et al. Nature 465(7298): 584-9 (2010)) (FIG. 3).

4.5 Design of miR-451 shRNA Mimics

One can design and express miR-451 shRNA mimics based on the features of the native gene encoding the miR-451 shRNA. In particular, the miR-451 architecture can be used to express miR-451 shRNA mimics from pol II promoter-based expression plasmids by using a variety of RNA pol II-based expression vectors or even from pol III promoter-based expression plasmids using pol III-dependent promoters. In certain embodiments, expression vectors may employ use of expression cassettes comprising the miR-451 shRNA mimic. In certain embodiments, expression vectors encoding miR-451 shRNA mimics may be based on CMV-based or MSCV-based vector backbones. In certain embodiments, expression vectors encoding miR-451 shRNA mimics may be based on self-inactivating lentivirus (SIN) vector backbones. Generally, appropriate vector backbones include vector backbones used in construction of expression vectors for conventional shRNAs, including mir-30 based shRNAs. Exemplary use of expression cassettes in construction of shRNA expression vectors also useful in the construction of expression cassettes encoding the miR-451 shRNA mimics of the invention are found in the following references: Gottwein E. and Cullen B. Meth. Enzymol. 427:229-243, 2007, Dickens et al., Nature Genetics, 39:914-921, 2007, Chen et al, Science 303: 83-86, 2004; Zeng and Cullen, RNA 9: 112-123, 2003, the contents of which are specifically incorporated herein by reference.

In certain embodiments, use the miR-451 shRNA mimics may employ precursor molecules comprised of flanking sequences. The precursor molecule is composed of any type of nucleic acid based molecule capable of accommodating such flanking sequences and the miR-451 shRNA mimic sequence. In certain embodiments, the methods for efficient expression of the miR-451 shRNA mimics involve the use of expression vectors comprising sequences encoding a precursor molecule, wherein the encoded precursor molecule is a miR-451 shRNA mimic in the context of flanking sequences. In some embodiments, the flanking sequences comprise primary miR-451 sequences. In some embodiments, the flanking sequences comprise primary sequences from an miRNA or miRNAs other than miR-451. In some embodiments the primary miRNA sequences used as, or as part of the flanking sequences may direct drosha cleavage of the miRNA. In general, this type of approach in using precursor miRNAs and the individual components of the precursor (flanking sequences and microRNA sequence) are provided in U.S. Publication No. 2008/0226553, which is specifically cited and incorporated by reference herein.

Figure 2:
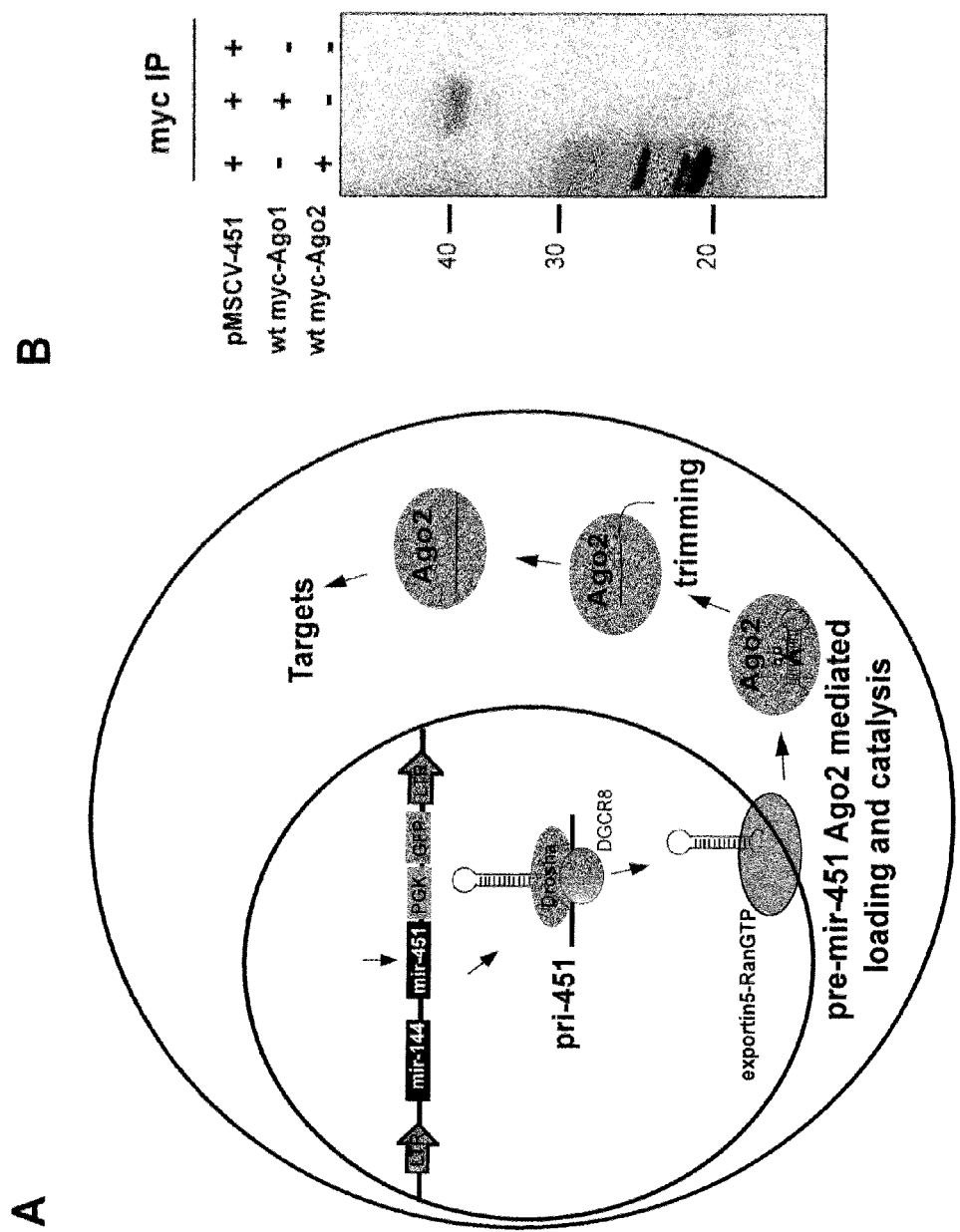

To investigate sequence versus structural requirements of miR-451 for entry into the alternative miRNA biogenesis pathway, we engineered structural mimics of miR-451 that might instead produce let-7c. At the concentration tested, these structural mimics were as potent as the native pre-let-7c in suppressing a GFP or luciferase reporter containing perfect let-7 complementary sites (FIGS. 1A-C). The miR-451 precursor could also be remodeled to express an shRNA that efficiently represses p53 (FIG. 1D)). We demonstrate that the primary transcript encoded from a transiently transfected miR-451 MSCV plasmid is processed to its mature form in human embryonic kidney 293 cells and only AGO2 is loaded with the mature form of the molecule (FIG. 2). The miR-451 expression plasmid is also processed in mouse embryonic fibroblast and mouse embryonic stems cells (Cheloufi et al., *Nature* 465(7298): 584-9 (2010)).

These results demonstrate that by engineering shRNA molecules that mimic the structure of miR-451, processing of these shRNA in mammalian cells is channeled into the alternative miRNA biogenesis pathway. In one aspect of the invention, miR-451 shRNA mimics may be used for suppression or silencing of particular expressed genes through a post-transcriptional mechanism by targeting the shRNA against the expressed mRNA. In another aspect of the invention, miR-451 mimics may be used for suppression or silencing of particular expressed genes through a transcriptional mechanism, by targeting the shRNA against introns or other non-coding regions of the target gene.

In one aspect of the invention, design of a miR-451 shRNA mimic may be based on the sequence of an siRNA targeted against the target gene. In another aspect, design of an miR-451 shRNA mimic may be based on any 21-23 nt sequence in the coding sequence of a target gene. In another aspect, design of a miR-451 shRNA mimic may be based on any 21-23 nt sequence in an intron or other non-coding region of a target gene. In particular, the miR-451 shRNA mimic comprises a sequence that is fully complementary to a 21 to 23 long nucleotide sequence in the target gene, or to the 21 to 23 nucleotide target sequence of the siRNA. In designing the miR-451 shRNA mimic, this fully complementary sequence is positioned within the shRNA, such that Ago2 processing of the shRNA and further trimming within the RISC complex generates an active silencing molecule comprising said fully complementary sequence.

In a non-limiting example, design of a miR-451 mimic shRNA targeting p53 is depicted in (FIG. 3). The resulting ~40 nt shRNA has a short stem and a tight loop and cannot be processed by DICER. Instead, it is cleaved by AGO2 and then further trimmed to generate the active strands.

In some embodiments of the invention, an shRNA comprises a first sequence of 21, 22, or 23 nucleotides fully complementary to a sequence in a non-coding target gene.

In some embodiments of the invention, an shRNA comprises a first sequence of 21, 22, or 23 nucleotides fully complementary to a sequence in a target long non-coding RNA.

In one aspect of the invention, an shRNA is provided comprising a first sequence of 21, 22 or 23 nucleotides fully complementary to a sequence in the coding region of a target gene, and a second sequence directly following the first sequence, wherein the second sequence is fully complementary to the sequence of the first 17 or 18 nucleotides counted from 5' end of the first sequence.

In some embodiments, the second sequence is at least 60%© complementary to the first 17 or 18 nucleotides counted from the 5' end of the first sequence. The second sequence may be at least 60% complementary to the first 17 or 18 nucleotides counted from the 5' end of the first sequence along its entire length, or along a portion of the first 17 or 18 nucleotides counted from the 5' end of the first sequence, provided the second sequence is capable of hybridizing with the first sequence under normal physiological conditions. In some embodiments, the second sequence may be from 60 to 99% complementary to the first 17 or 18 nucleotides counted from the 5' end of the first sequence. The second sequence may be 60%, 65%, 70%, 75%, 80%, 85%, 90%, or 95% complementary to the first 17 or 18 nucleotides counted from the 5' end of the first sequence.

In some embodiments, an shRNA comprises a first sequence of 21, 22 or 23 nucleotides which is complementary to a sequence in a target mRNA molecule, gene, or long non-coding RNA and a second sequence directly following the first sequence, wherein the second sequence is complementary to the sequence of the first 17 or 18 nucleotides counted from the 5' end of the first sequence. In some embodiments the first sequence is at least 60% complementary to a sequence in a target mRNA molecule, gene, or long non-coding RNA. The first sequence may be at least 60% complementary to a sequence in a target mRNA molecule or gene along its entire length, or along portions of its length, provided at least 12 nucleotides are complementary between the two sequences, continuously or non-continuously, and provided the first sequence is capable of hybridizing with the sequence in the target mRNA molecule, gene, or long non-coding RNA under normal physiological conditions. In some embodiments, the first sequence may be from 60 to 99% complementary to a sequence in a target mRNA molecule, gene, or long non-coding RNA. The first sequence may be 60%, 65%, 70%, 75%, 80%, 85%, 90%, or 95% complementary to a sequence in a target mRNA molecule, gene, or long non-coding RNA.

In some embodiments, an shRNA of the invention may be an isolated shRNA.

In various embodiments of the instant shRNA, the last 3 nucleotides, or alternatively the last 4 nucleotides, of the first sequence form a loop region in the short hairpin molecule.

In various embodiments of the instant shRNA, the shRNA has a 1 nucleotide overhang at its 3' end, or alternatively a 2, 3 or more than 3 nucleotide overhang at its 3' end.

In various embodiments of the instant shRNA, the shRNA has a 1 nucleotide overhang at its 5' end, or alternatively a 2, 3 or more than 3 nucleotide overhang at its 5' end.

In an embodiment of the instant shRNA, the shRNA has no 3' or 5' overhang.

In an embodiment of the instant shRNA, the shRNA consists of a first sequence of 21, 22 or 23 nucleotides fully complementary to a sequence in the coding region of a target gene, and a second sequence directly following the first sequence, wherein the second sequence is fully complementary to the sequence of the first 17 or 18 nucleotides counted from the 5' end of the first sequence.

Another aspect of the invention provides for design of non-naturally occurring miRNAs based on structural mimics of miR-451 precursors. In certain embodiments, such structural miRNA mimics of miR-451, or an expression vector or library of expression vectors encoding such structural mimics can be introduced into different genetic backgrounds of mammalian cells, in particular in cells deficient of the canonical pathway enzymes, such as dicer, to screen for and identify such miRNAs capable of rescuing the null phenotype and the functional roles of such miRNAs in contributing to the phenotype.

Another aspect of the invention provides for the design of non-naturally occurring miRNA mimics of miR-451 precursors that comprise the guide sequence of a naturally occurring canonical shRNA. Certain embodiments of the invention comprise an expression vector or libraries of expression vectors encoding such shRNAs. In some embodiments, an shRNA of the invention may be designed to target a sequence normally targeted by a canonical miRNA. In some embodiments, the shRNA, or a library of shRNAs may be expressed in cells deficient in one or more of the canonical pathway enzymes such as dicer, to screen for and/or identify such miRNAs capable of rescuing the null phenotype, or part of the null phenotype, and/or the functional roles of such miRNAs in contributing to a phenotype or a part of a phenotyope. One of skill in the art will understand that miRNAs are not always fully complementary to their target sequences, including those in the 3'UTR of a target mRNA. In some embodiments, non-naturally occurring miRNA mimics of miR-451 precursors comprise the guide sequence of a canonical shRNA that is between 60 and 100% complementary to one or more target sequences. In some embodiments a guide sequence may be 60, 65, 75, 80, 85, 90, 95, or 99% complementary to its target sequence(s). One of skill in the art will understand that a guide sequence may have multiple target sequences for which it might have differing complementarity.

In one aspect of the invention, a non-naturally occurring miRNA is provided comprising a first sequence of 21, 22 or 23 nucleotides corresponding to the entire mature sequence, or a portion of that sequence, of a mammalian miRNA other than miR-451, and a second sequence directly following the first sequence, wherein the second sequence is fully complementary to the sequence of the first 17 or 18 nucleotides counted from the 5' end of the first sequence. The skilled practitioner will appreciate that the mature sequence of a mammalian miRNA alternatively may be identified as the sequence of the guide strand, or guide sequence for that miRNA.

In one aspect of the invention, an shRNA is provided comprising a first sequence of 19, 20 or 21 nucleotides fully complementary to a sequence in a target gene, having a sequence other than the mature sequence of miR-451, and a second sequence directly following the first sequence, wherein the second sequence is fully complementary to the sequence of the first 15 or 16 nucleotides counted from the 5' end of the first sequence.

In one aspect of the invention, an shRNA is provided comprising a first sequence of 21, 22 or 23 nucleotides complementary to a sequence in a target gene, and a second sequence directly following the first sequence, wherein the second sequence is fully complementary to the sequence of the first 17 nucleotides counted from the 5' end of the first sequence.

In one aspect of the invention, an shRNA is provided comprising a first sequence of 21, 22 or 23 nucleotides fully complementary to a sequence in the coding region of a target gene, and a second sequence directly following the first sequence, wherein the second sequence is complementary to the sequence of the first 17 nucleotides counted from the 5' end of the first sequence.

In one aspect of the invention, an shRNA is provided comprising a first sequence of 21, 22 or 23 nucleotides complementary to a sequence in a target gene, having a sequence other than the mature sequence of miR-451, and a second sequence directly following the first sequence, wherein the second sequence is complementary to the sequence of the first 17 nucleotides counted from the 5' end of the first sequence.

In some embodiments, the first sequence of 21, 22 or 23 nucleotides is fully complementary to a sequence in a target gene.

In some embodiments, the first sequence of 21, 22 or 23 nucleotides is complementary to a coding region of the target gene.

In some embodiments, the first sequence of 21, 22 or 23 nucleotides is complementary to a sequence in an mRNA molecule encoded by the gene, wherein the sequence in the mRNA molecule is present in the sequence of the target gene.

In some embodiments, the first sequence of 21, 22 or 23 nucleotides is complementary to a 3' untranslated region (UTR) sequence in an mRNA molecule encoded by the gene, wherein the 3' UTR sequence in the mRNA molecule is present in the sequence of the target gene.

In some embodiments, the second sequence directly following the first sequence is fully complementary to the sequence of the first 18 nucleotides counted from the 5' end of the first sequence. In some embodiments, the shRNA consists of from 38 to 50 nucleotides.

In one aspect of the invention, an shRNA is provided having the structure

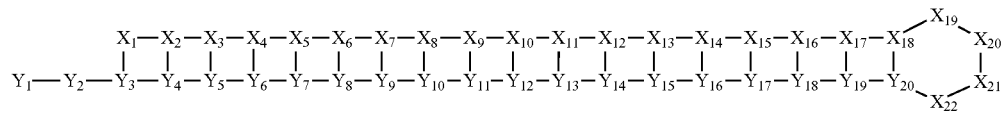

wherein $X_2$ to $X_{22}$ are nucleotides complementary to a sequence in a target gene, and are in a sequence other than the mature sequence of miR451; $Y_4$ to $Y_{20}$ are nucleotides complementary to $X_2$ to $X_{18}$; and $X_1$, $Y_1$, $Y_2$, and $Y_3$, are nucleotides that may be present or absent, wherein, $X_1$ and $Y_1$, when present, may be complementary or not complementary In various embodiments of the instant non-naturally occurring miRNA, the last 3 nucleotides, or alternatively the last 4 nucleotides, of the first sequence form a loop region in the short hairpin molecule.

In various embodiments of the instant non-naturally occurring miRNA, the non-naturally occurring miRNA has a 1 nucleotide overhang at its 3' end, or alternatively a 2, 3 or more than 3 nucleotide overhang at its 3' end.

In various embodiments of the instant non-naturally occurring miRNA, the non-naturally occurring miRNA has a 1 nucleotide overhang at its 5' end, or alternatively a 2, 3 or more than 3 nucleotide overhang at its 5' end.

In an embodiment of the instant non-naturally occurring miRNA, the non-naturally occurring miRNA has no 3' or 5' overhang.

In some embodiments, the shRNA of the invention is a synthetic shRNA.

As non-limiting examples, in certain embodiments the instant non-naturally occurring miRNA can comprise a sequence, selected from the mature sequence of human miR-18b (uaaggugcaucuagugcaguug) (SEQ ID NO: 12) of 21, 22 or 23 nucleotides: for example, uaaggugcaucuagugcaguu (SEQ ID NO: 13), uaaggugcaucuagugcaguua (SEQ ID NO: 14), uaaggugcaucuagugcaguuag (SEQ ID NO: 15), aaggugcaucuagugcaguuag (SEQ ID NO: 16), aggugcaucuagugcaguuag (SEQ ID NO: 17). In certain embodiments the instant non-naturally occurring miRNA can comprise a sequence, selected from the mature sequence of human miR-21(uagcuuaucagacugauguuga) (SEQ ID NO: 18) of 21 or 22 nucleotides: for example, uagcuuaucagacugauguug (SEQ ID NO: 19), uagcuuaucagacugauguuga (SEQ ID NO: 20), agcuuaucagacugauguuga (SEQ ID NO: 21). In other embodiments, non-naturally occurring miRNA can comprise a sequence of 21, 22 or 23 nucleotides selected from the mature sequence of any other human or mammalian miRNA, wherein such sequences are readily available through public databases, such as miRBase, (Griffiths-Jones et al., miRBase: tools for microRNA genomics, *NAR,* 2008, Vol. 36, Database issue D154-D158), accessible at www.mirbase.org, such mature miRNA sequences available on miRBase specifically incorporated herein by reference.

In certain preferred embodiments, the instant non-naturally occurring miRNA can comprise a sequence, selected from the mature sequence of a human or mammalian miRNA with known involvement in cancer and other diseases, or those with known involvement in development and differentiation, for example such miRNAs, and mature sequences thereof, identified in United States patents and Patent Publications Nos., U.S. Pat. Nos. 7,232,806, 7,307,067, 7,670,840, US 2010/0048674 (Feb. 25, 2010), US 2007/0072204 (Mar. 29, 2007), US 2009/0124566 (May 14, 2009), US 2009/0176723 (Jul. 9, 2009), US 2009/0186353 (Jul. 23, 2009) and US 2009/0286242 (Nov. 19, 2009), the contents of which are herein specifically incorporated by reference.

In certain embodiments, a non-naturally occurring miRNA is provided comprising a first sequence of 21, 22 or 23 nucleotides corresponding to the entire sequence of the passenger strand of a mammalian miRNA, or a portion of that sequence, and a second sequence directly following the first sequence, wherein the second sequence is fully complementary to the sequence of the first 17 or 18 nucleotides counted from the 5' end of the first sequence. In certain embodiments, the instant non-naturally occurring miRNA can comprise a sequence of 21, 22 or 23 nucleotides selected from the sequence of the passenger strand of any human or mammalian miRNA, wherein such passenger strand sequences, or annotations defining such sequences, are readily available through public databases, such as miRBase, (Griffiths-Jones et al., miRBase: tools for microRNA genomics, *NAR,* 2008, Vol. 36, Database issue D154-D158), accessible at www.mirbase.org, wherein such sequences or annotations identifying such sequences, and available on miRBase, are specifically incorporated herein by reference. Also included in the invention is an isolated non-mammalian cell comprising the shRNAs described herein. The cells may be those of vertebrate organisms, or non-vertebrate organisms such as insects. The cells may be those of fish (e.g. those of the *Fugu* genus or the *Danio* genus), frogs (e.g. those of the *Xenopus* genus), round worms (e.g, those of the *Caenorhabdis genus*), flies (such as the *Drosophila* genus), or others. Another aspect of the invention provides a non-human animal comprising the cell described above. In certain embodiments, the non-human animal may be a chimeric animal, some of whose somatic or germ cells comprising the shRNAs described herein. Alternatively, the non-human animal may be a transgenic animal, all of whose somatic or germ cells comprise the shRNAs described herein. Thus, transgenic animals whose genomes comprise a sequence encoding the shRNAs of the invention are also provided.

4.6 Vectors

In certain embodiments, expression vectors encoding miR-451 shRNA mimics may be based on CMV-based or MSCV-based vector backbones. In certain embodiments, expression vectors encoding miR-451 shRNA mimics may be based on self-inactivating lentivirus (SIN) vector backbones. Generally, appropriate vector backbones include vector backbones used in construction of expression vectors for conventional shRNAs, including mir-30 based shRNAs. Exemplary vector backbones and methodologies for construction of expression vectors suitable for use with the miR-451 shRNA mimics of this invention, and methods for introducing such expression vectors into various mammalian cells are found in the following references: Premsrurit P K. et al., *Cell,* 145(1):145-158, 2011, Gottwein E. and Cullen B. *Meth. Enzymol.* 427:229-243, 2007, Dickens et al., *Nature Genetics,* 39:914-921, 2007, Chen et al., *Science* 303: 83-86, 2004; Zeng and Cullen, *RNA* 9: 112-123, 2003, the contents of which are specifically incorporated herein by reference.

The vectors can be targeting vectors, such as those using flp recombination into the colA locus allowing single copy integration. Other targeting sites in the mouse genome include but are not limited to ROSA26 and HPRT. Additionally, transposase may be used to introduce mimics into the genome of an animal or the cell of an animal. See, Premsrurit P K. et al., *Cell,* 145(1):145-158, (2011), the contents of which are specifically incorporated herein by reference.

The vectors described in International application no. PCT/US2008/081193 (WO 09/055,724) and methods of making and using the vectors are incorporated herein by reference. The disclosure provided therein illustrates the general principles of vector construction and expression of sequences from vector constructs, and is not meant to limit the present invention.

shRNAs can be expressed from vectors to provide sustained silencing and high yield delivery into almost any cell type. In a certain embodiment, the vector is a viral vector. Exemplary viral vectors include retroviral, including lentiviral, adenoviral, baculoviral and avian viral vectors. The use of viral vector-based RNAi delivery not only allows for stable single-copy genomic integrations but also avoids the non-sequence specific response via cell-surface toll-like receptor 3 (TLR3), which has raised many concerns for the specificity of siRNA mediated effects. In one embodiment of the present invention, a pool of shRNAs is introduced into murine HSCs using a vector known in the art.

Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317, R-2, R-AM, PA12, T19-14x, VT-19-17-H2, RCRE, RCRIP, GP+E−86, GP+envAm12, and DAN cell lines as described in Miller, *Human Gene Therapy* 1:5-14 (1990), which is incorporated herein by reference in its entirety. The vector can transduce the packaging cells through any means known in the art. A producer cell line generates infectious retroviral vector particles which include polynucleotide encoding a DNA replpication protein. Such retroviral vector particles then can be employed, to transduce eukaryotic cells, either in vitro or in vivo. The transduced eukaryotic cells will express a DNA replpication protein.

In certain embodiments, cells can be engineered using an adeno-associated virus (AAV). AAVs are naturally occurring defective viruses that require helper viruses to produce infectious particles (Muzyczka, N., *Curr. Topics in Microbiol.*

*Immunol.* 158:97 (1992)). It is also one of the few viruses that can integrate its DNA into nondividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377. For example, an AAV vector can include all the sequences necessary for DNA replication, encapsidation, and host-cell integration. The recombinant AAV vector can be transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells.

In certain embodiments, cells can be engineered using a lentivirus and lentivirus based vectors. Such an approach is advantageous in that it allows for tissue-specific expression in animals through use of cell type-specific pol II promoters, efficient transduction of a broad range of cell types, including nondividing cells and cells that are hard to infect by retroviruses, and inducible and reversible gene knockdown by use of tet-responsive and other inducible promoters. Methods for expressing shRNAs by producing and using lentivirus engineered cells are known in the art. For exemplary descriptions of such methods, see for example, Stegmeier F. et al., *Proc Acad Sci USA* 2005, 102(37):13212-13217, Klinghoffer et al., *RNA* 2010, 16:879-884, the contents of which are specifically incorporated herein. Efficient production of replication-incompetent recombinant lentivirus may be achieved, for example, by co-tranfection of expression vectors and packaging plasmids using commercially available packaging cell lines, such as TLA-HEK293™, and packaging plasmids, available from Thermo Scientific/Open Biosystems, Huntsville, Ala.

Essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded shRNA. Other methods known in the art for introducing nucleic acids to cells can be used, such as lipid-mediated carrier transport, chemical mediated transport, such as calcium phosphate, and the like. Thus the shRNA-encoding nucleic acid construct can be introduced along with components that perform one or more of the following activities: enhance RNA uptake by the cell, promote annealing of the duplex strands, stabilize the annealed strands, or otherwise increase inhibition of the target gene.

Expression of endogenous miRNAs is controlled by RNA polymerase II (Pol II) promoters. It has been shown that shRNAs are also most efficiently driven by Pol II promoters, as compared to RNA polymerase III promoters (Dickins et al., 2005, *Nat. Genet.* 39: 914-921). Therefore, in a certain embodiment, the coding sequence of the RNAi molecule is controlled by an inducible promoter or a conditional expression system, including, without limitation, RNA polymerase type II promoters. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies. See International Patent Application PCT/US2003/030901 (Publication No. WO 2004-029219 A2) and Fewell et al., 2006, *Drug Discovery Today* 11: 975-982, for an exemplary description of inducible shRNA.

To facilitate the monitoring of the target gene knockdown, cells harboring the RNAi-expressing construct can additionally comprise a marker or reporter construct, such as a fluorescent construct. The reporter construct can express a marker, such as green fluorescent protein (GFP), enhanced green fluorescent protein (EGFP), Renilla Reniformis green fluorescent protein, GFPmut2, GFPuv4, yellow fluorescent protein (YFP), such as VENUS, enhanced yellow fluorescent protein (EYFP), cyan fluorescent protein (CFP), enhanced cyan fluorescent protein (ECFP), blue fluorescent protein (BFP), enhanced blue fluorescent protein (EBFP), citrine and red fluorescent protein from discosoma (dsRED). Other suitable detectable markers include chloramphenicol acetyl-transferase (CAT), luminescent proteins such as luciferase lacZ (β-galactosidase) and horseradish peroxidase (HRP), nopaline synthase (NOS), octopine synthase (OCS), and alkaline phosphatase. The marker gene can be separately introduced into the cell harboring the shRNA construct (e.g., co-transfected, etc.). Alternatively, the marker gene can be on the shRNA construct, and the marker gene expression can be controlled by the same or a separate translation unit, for example, by an IRES (internal ribosomal entry site). In one aspect of the invention, marker genes can be incorporated into "sensor" expression vectors for use in high throughput methods for determining the knockdown efficiency of miR-451 shRNA mimics targeted against particular genes and for identifying the most potent target sequences for a particular target gene. Such methods, including the design and use of plasmids and reporter constructs for testing the potency of particular shRNA molecules, here useful for testing the potency of the miR-451 shRNA mimics are described in PCT publication Fellman et al., WO/2009/055724, the contents of which is herein specifically incorporated by reference in its entirety.

Reporters can also be those that confer resistance to a drug, such as neomycin, ampicillin, bleomycin, chloramphenicol, gentamycin, hygromycin, kanamycin, lincomycin, methotrexate, phosphinothricin, puromycin, doxycycline, and tetracyclin. Reporters can also be lethal genes, such as herpes simplex virus-thymidine kinase (HSV-TK) sequences, as well as sequences encoding various toxins including the diphtheria toxin, the tetanus toxin, the cholera toxin and the pertussis toxin. A further negative selection marker is the hypoxanthine-guanine phosphoribosyl transferase (HPRT) gene for negative selection in 6-thioguanine.

To facilitate the quantification of specific shRNAs in a complex population of cells infected with a library of shRNAs, each shRNA construct can additionally comprise a barcode. A barcode is a unique nucleotide sequence (generally a 19-mer), linked to each shRNA. The barcode can be used to monitor the abundance of each shRNA via microarray hybridization (Fewell et al., 2006, *Drug Discovery Today* 11: 975-982). In a certain embodiment, each shRNA construct also comprises a unique barcode. For more information on the use of barcodes in shRNA pooled analyses, see WO 04/029219, Bernards et al., 2006, *Nature Methods* 3: 701-706, and Chang et al., 2006, *Nature Methods* 3: 707-714.

4.7 Methods of Treatment

In certain embodiments, the invention provides a composition formulated for administration of miR-451 shRNA mimics in vivo to a subject, such as a human or veterinary subject. A composition so formulated can comprise a stem cell comprising a nucleic acid construct encoding a miR-451 shRNA mimic designed to decrease the expression of a target gene. A composition can also comprise a pharmaceutically acceptable excipient.

For example, the miR-451 shRNA mimic can be reliably expressed in vivo in a variety of cell types. In certain embodiments the cells are administered in order to treat a condition. There are a variety of mechanisms by which shRNA expressing cells can be useful for treating cancer and other diseases. For example, a condition can be caused, in part, by a population of cells expressing an undesirable gene. These cells can be ablated and replaced with administered cells comprising shRNA that decreases expression of the undesirable gene. An shRNA can be targeted to essentially any gene, the decreased expression of which can be helpful in treating cancer or another disease.

Any suitable cell can be used. For example, cells to be transfected can be essentially any type of cell for implantation into in a subject. The cell having the target gene can be germ line or somatic, totipotent or pluripotent, dividing or non-dividing, parenchymal or epithelial, immortalized or transformed, or the like. The cell can be a stem cell or a differentiated cell. After transfection, stem cells can be administered to a subject, or cultured to form differentiated stem cells (e.g., embryonic stem cells cultured to form neural, hematopoietic or pancreatic stem cells) or cultured to form differentiated cells.

Stem cells can be stem cells recently obtained from a donor, and in certain embodiments, the stem cells are autologous stem cells. Stem cells can also be from an established stem cell line that is propagated in vitro. Suitable stem cells include embryonic stems and adult stem cells, whether totipotent, pluripotent, multipotent or of lesser developmental capacity. Stem cells can be derived from mammals, such as rodents (e.g. mouse or rat), primates (e.g. monkeys, chimpanzees or humans), pigs, or ruminants (e.g. cows, sheep and goats). Examples of mouse embryonic stem cells include: the JM1 ES cell line described in M. Qiu et al., *Genes Dev* 9, 2523 (1995), and the ROSA line described in G. Friedrich, P. Soriano, *Genes Dev* 5, 1513 (1991), and mouse ES cells described in U.S. Pat. No. 6,190,910. Many other mouse ES lines are available from Jackson Laboratories (Bar Harbor, Me.). Examples of human embryonic stem cells include those available through the following suppliers: Arcos Bioscience, Inc. Foster City, Calif.; CyThera, Inc., San Diego, Calif.; ES Cell International, Melbourne, Australia; Geron Corporation, Menlo Park, Calif.; University of California, San Francisco, Calif.; and Wisconsin Alumni Research Foundation, Madison, Wis. In addition, examples of embryonic stem cells are described in the following U.S. patents and published patent applications: U.S. Pat. Nos. 6,245,566; 6,200,806; 6,090,622; 6,331,406; 6,090,622; 5,843,780; 20020045259; 20020068045. Examples of human adult stem cells include those described in the following U.S. patents and patent applications: U.S. Pat. Nos. 5,486,359; 5,766,948; 5,789,246; 5,914,108; 5,928,947; 5,958,767; 5,968,829; 6,129,911; 6,184,035; 6,242,252; 6,265,175; 6,387,367; 20020016002; 20020076400; 20020098584; and, for example, in PCT publication WO 01/11011. In certain embodiments, a suitable stem cell can be derived from a cell fusion or dedifferentiation process, such as described in U.S. patent application 20020090722, in PCT publications WO 02/38741, WO 01/51611, WO 99/63061, and WO 96/07732.

Transfected cells can also be used in the manufacture of a medicament for the treatment of subjects. Examples of pharmaceutically acceptable excipients include matrices, scaffolds, or other substrates to which cells can attach (optionally formed as solid or hollow beads, tubes, or membranes), as well as reagents that are useful in facilitating administration (e.g. buffers and salts), preserving the cells (e.g. chelators such as sorbates, EDTA, EGTA, or quaternary amines or other antibiotics), or promoting engraftment. Cells can be encapsulated in a membrane or in a microcapsule. Cells can be placed in microcapsules composed of alginate or polyacrylates. (Sugamori et at (1989) *Trans. Am. Soc. Artif. Intern. Organs* 35:791; Levesque et al. (1992) *Endocrinology* 130: 644; and Lim et al. (1992) *Transplantation* 53:1180).

Additional methods for encapsulating cells are known in the art. (Aebischer et al. U.S. Pat. No. 4,892,538; Aebischer et al. U.S. Pat. No. 5,106,627; Hoffman et al. (1990) Expt. Neurobiol. 110:39-44; Jaeger et al. (1990) *Prog. Brain Res.* 82:4146; and Aebischer et al. (1991) *J. Biomech. Eng.* 113: 178-183, U.S. Pat. No. 4,391,909; U.S. Pat. No. 4,353,888; Sugamori et al. (1989) *Trans. Am. Artif Intern. Organs* 35:791-799; Sefton et al. (1987) *Biotechnol. Bioeng.* 29:1135-1143; and Aebischer et al. (1991) *Biomaterials* 12:50-55).

The site of implantation of cell compositions can be selected by one of skill in the art depending on the type of cell and the therapeutic objective. Exemplary implantation sites include intravenous or intraarterial administration, administration to the liver (via portal vein injection), the peritoneal cavity, the kidney capsule or the bone marrow.

In certain embodiments, the invention provides for modification and in viva delivery of miR-451 shRNA mimics as synthetic RNAi molecules. Modification and in vivo delivery of synthetic RNAi molecules, including shRNAs incorporating modified nucleotides, such as those with chemical modifications to the 2'-OH group in the ribose sugar backbone, such as 2'-O-methyl (2'OMe), 2'-fluoro (2'F) substitutions, and those containing 2'OMe, or 2'F, or 2'-deoxy, or "locked nucleic acid" (LNA) modifications can be accomplished as described in U.S. Pat. Nos., U.S. Pat. Nos. 6,627,616, 6,897, 068, 6,379,966; in U.S. Patent Application Publication Nos. US. 2005/0107325 (May 19, 2005), US 2007/0281900 (Dec. 6, 2007) and US 2007/0293449 (Dec. 20, 2007); and in Vorhies and Nemunaitis J J, *Methods Mol Biol.* 2009; 480: 11-29, López-Fraga M et al., *Infect Disord Drug Targets.* 2008 December; 8(4):262-73, Watts et al., *Drug Discov Today.* 2008 October; 13(19-20):842-55, Lu and Woodle, *Methods Mol Biol.* 2008; 437:93-107, de Fougerolles et al., *Hum Gene Ther,* 2008 February; 19(2):125-32, Rossi J J, *Hum Gene Ther.* 2008 April; 19(4):313-7, Belting M and Wittrup A. *Methods Mol Biol.* 2009; 480:1-10, Pushparaj et al., *J. Dent. Res.* 2008; 87: 992-1003, Shrivastava and Srivastava, *Biotechnol J.* 2008 March; 3(3):339-53, and Raemdonck K. et al., *Drug Discov Today,* 2008 November; 13(21-22):917-31, Castanotto D & Rossi J J, *Nature* 2009 January; 457:426-433, Davis M et al., Nature advance online publication (21 Mar. 2010) doi:10.1038/nature08956, each of which are incorporated by reference in their entireties.

4.8 Screening Methods

Constructs encoding miR-451 shRNA mimics or libraries of such constructs can be introduced into intact cells/organisms and can be used in screening, such as high throughput screening (HTS). For example, by using miR-451 shRNA mimics or libraries of such mimics to can be assessed. Similarly, potential targets for pharmaceuticals can be identified or studied using such methods. A panel of miR-451 shRNA mimics that affect target gene expression by varying degrees may be used. In particular, it may be useful to measure any correlation between the degree of gene expression decrease and a particular phenotype.

Libraries of miR-451 shRNA mimics can be produced using methods known in the art. For example, libraries of miR-451 shRNA mimics can based on existing libraries, such as existing shRNA libraries. Existing materials and methods for design and construction of expression cassettes, selection and modification of vectors and vector backbones, library construction, design of target sequences, and library validation, as applied to conventional shRNA libraries may be applied in the construction of libraries comprised of the miR-451 shRNA mimics of the present invention. As non-limiting examples, such materials and methods are described in Chang et al. Nature Meth. 3:707-714 (2006), PCT publication Fellman et al., WO/2009/055724, the contents of which are specifically incorporated herein by reference.

In certain aspects, the invention provides methods for screening/evaluating gene function in vivo. A cell containing a construct for expression of a miR-451 shRNA mimic may be introduced into an animal and a phenotype may be assessed to determine the effect of the decreased gene expression. An entire animal may be generated from such cells (e.g., ES cells) containing the miR-451 shRNA mimic construct. A phenotype of the animal may be assessed. The animal may be essentially any experimentally tractable animal such as a non-human primate, a rodent, a canine, a feline, etc. Populations of animals expressing different members of a library of miR-451 shRNA mimics may also be generated. The phenotypes of such animals may be assessed to determine, for example, the effect of a target gene on a disease phenotype (e.g. tumor initiation or growth), stem cell differentiation, drug sensitivity (e.g. sensitivity of tumor cells to chemotherapeutic drugs), susceptibility to a viral, bacterial or other infections, or any other phenotype of interest, including disease phenotypes.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

5. EXAMPLES OF THE INVENTION

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

5.1 Example 1

Identification of a Non-Canonical MicroRNAs Biogenesis Pathway

5.1.1 Mature miR-451 Expression Depends on Ago2 Catalysis

To investigate the evolutionary pressure to conserve Argonaute enzymatic activity, we engineered a mouse with catalytically inactive Ago2 alleles. Homozygous mutants died shortly after birth with an obvious anemia. (Cheloufi et at, Nature 465(7298): 584-9 (2010)). Our results suggested that miRNA directed target cleavage might prove important for erythrocyte maturation. As a step toward identifying such a target, we profiled miRNAs expressed in the liver, one of the fetal hematopoietic sites. Deep sequencing from wild-type animals and Ago2$^{ADH}$ homozygotes revealed that virtually all microRNAs were present at nearly identical levels. However, one miRNA, miR-451, represented 11% of all miRNA reads in normal fetal liver but was dramatically reduced in the mutants (FIG. 4).

Previous studies have demonstrated a strong dependency of the development of pro-E into basophilic erythroblasts on the expression of miR-45137. Together, miR-451 and miR-144 form a microRNA cluster with robust expression in erythroid cells. This pattern can be explained in part based upon the presence of regulatory sites for the GATA-1 zinc finger transcription factor, which acts as a master regulator of eythroid differentiation 38. The regulatory circuit seems to be intact in Ago2ADH animals, since we observe no changes in the levels of pri-mir144-451 in homozygous mutants (FIG. 4B). This strongly pointed to an impact of catalysis on miR-451 maturation rather than miR-451 expression.

MicroRNA biogenesis occurs via a two-step processing pathway wherein Drosha initially cleaves the primary microRNA transcript to liberate a hairpin pre-miRNA 39. This is exported to the cytoplasm and recognized and cleaved by Dicer to yield the mature duplex, which is loaded into Ago. The passenger strand is removed through unknown mechanisms to yield a complex ready for target recognition.

Figure 4C:
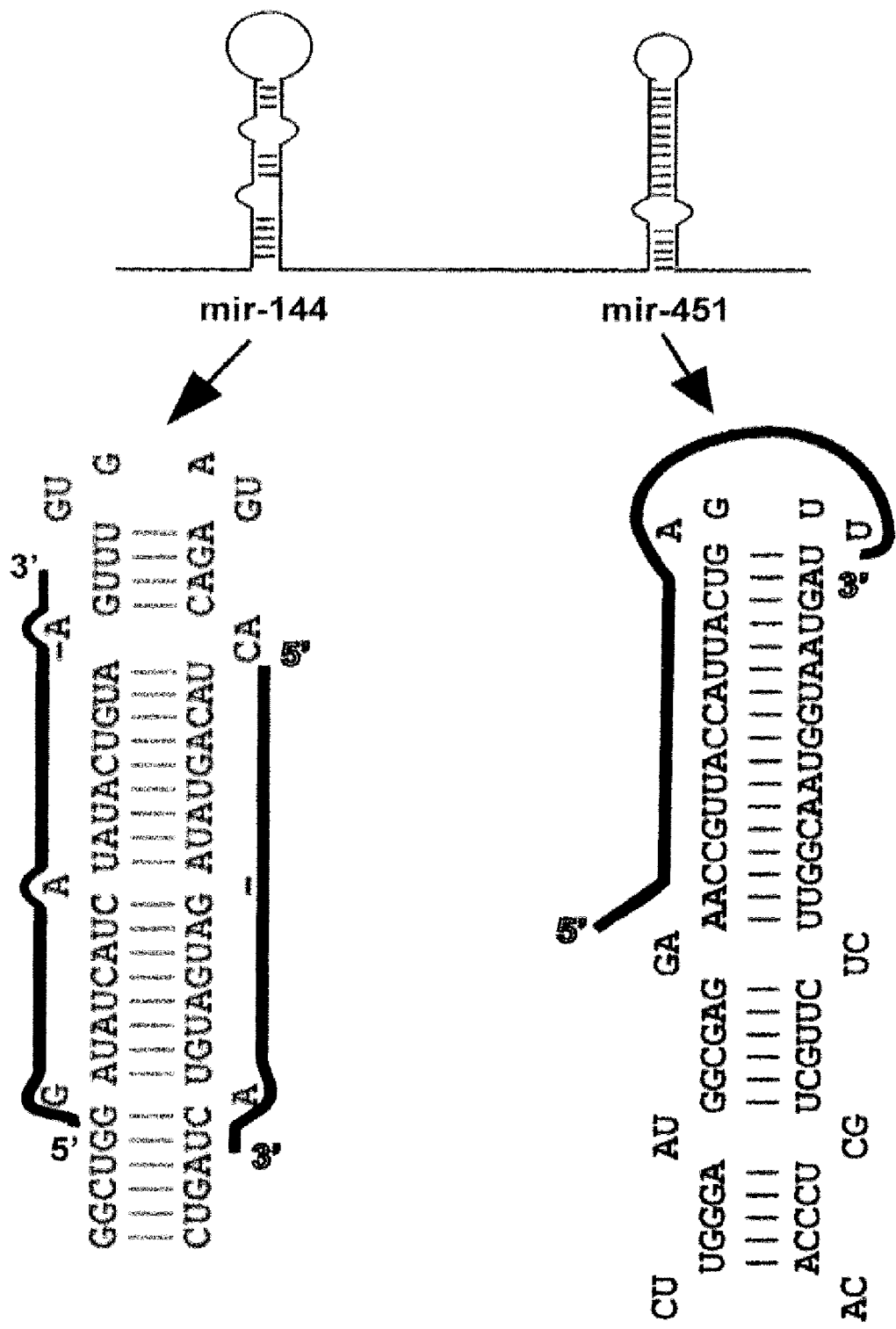

An examination of the miR-451 precursor and its mature strand revealed an unusual feature. As annotated, the 6 terminal nucleotides of the 23 nt long mature miR-451 span the loop region and extend into the complementary strand of the hairpin precursor. This arrangement appears incompatible with the well-studied enzymatic activities of Drosha and Dicer, which would normally liberate the mature microRNA mapping to the stem only (FIG. 4C). We therefore explored the possibility that miR-451 might adopt an unusual mode of biogenesis.

5.1.3 Non-Canonical Biogenesis of miR-451

We began by assessing the dependency of miR-451 on Drosha. We created a construct, which drives the expression of the miR-144/451 precursor from a strong viral promoter and introduced this into MEF homozygous for a conditional Drosha allele. Following activation of Cre-ER and Drosha loss of function, we noted a 20-fold reduction in levels of mature miR-451. This was even more dramatic than the effect on a miRNA, let-7c, with a well-established dependency on canonical processing factors (FIG. 5A). We also assessed the ability of Drosha to liberate pre-miR-451 in vitro. Drosha complexes were affinity purified from human 293T cells and mixed with in vitro synthesized fragments of pri-miR-451 or pri-miR-144. In both cases, bands of the appropriate size for the pre-miRNA were observed (FIG. 5B). In the case of pri-miR-451 processing the 5' flank of the transcript folds into an additional hairpin, which may be released by Drosha to give additional fragments. As a result, only one flank was observed. The identities of pre-miRNA bands were confirmed by Northern blotting with oligonucleotide probes corresponding to the predicted species (FIG. 5C). Considered together, these experiments provide both genetic and biochemical support for Drosha catalyzing the excision of pre-miR-451 from its primary transcript.

Pre-miR-451 has an unusually short, 17 nt stem region. Previous studies indicate that this is too short to be efficiently recognized and processed by Dicer (Siolas et al., 2004). We therefore examined the role of Dicer in miR-451 maturation. We introduced the pre-miR-451 expression vector into ES cells that are homozygous for Dicer conditional alleles and express Cre-ER. While acute Dicer loss caused a roughly 80-fold reduction in a control ES cell microRNA (miR-294), miR-451 levels did not change (FIG. 5D). A pure population of continuous Dicer-null ES cells showed more than a 500-fold reduction in conventional microRNA, whereas levels of miR-451 were unaffected (FIG. 2B). We also confirmed this results using northern blot analysis of dicer nulls ES cells transiently expressing the miR-451 precursor (FIGS. 1A-B). Finally, we incubated synthetic miR-451 pre-miRNA with recombinant Dicer and observed no mature cleavage products, though pre-let-7 was efficiently processed. Thus, conversion of pre-miR-451 into a mature miRNA proceeds independently of Dicer. We therefore strove to identify an alternative maturation pathway.

5.1.4 Ago2 Catalysis is Required for miR-451 Biogenesis

Figure 6:
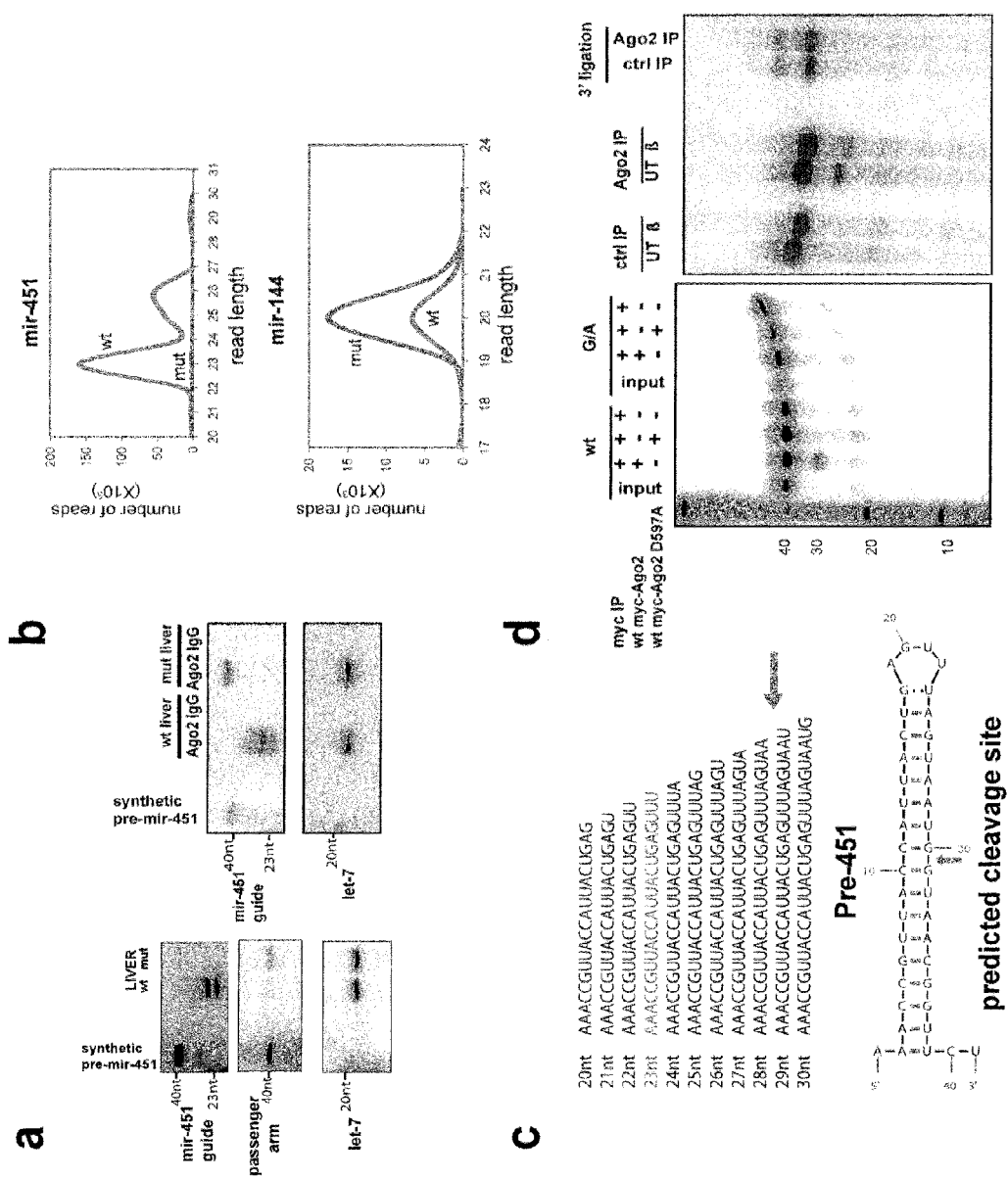

A By Northern blotting, we examined miR-451 species in wild-type and Ago2ADH mutant livers. This confirmed loss of the mature miRNA in the mutant animals. However, we noted the appearance of an ~40 nt band that co-migrated with a synthetic pre-miR-451 and hybridized to probes to its 5' and 3' arms (FIG. 6A). This indicated accumulation of the Drosha cleavage product in mutant animals. Notably, the same bands seen in total RNA were also detected in Ago2 immunoprecipitates (FIG. 6A). This demonstrated the direct loading of the pre-miRNA into Ago2 and raised the possibility that the Ago2 catalytic center might help to catalyze the maturation of this microRNA.

The well-established biochemical properties of Ago2 predict that it would cleave a loaded pre-miR-451 after its 30th base. We searched for evidence of such an intermediate in fetal liver small RNA libraries encompassing an expanded size range. Plotting a size distribution of reads corresponding to a conventional miRNA, miR-144, gave the expected pattern, a sharp peak at ~20 nt. In contrast, miR-451 showed a heterogeneous size distribution, exclusively because of variation at its 3' end. One abundant species corresponded precisely to the predicted Ago cleavage product (FIGS. 6B-C).

We confirmed the capacity of Ago2 to load and cleave pre-miR-451 using in vitro assays (FIG. 5D). Wild-type or catalytically inactive Ago2 complexes, or Ago1 complexes (FIGS. 2B, 6D) were affinity purified from 293T cells and mixed with 5'-end labeled pre-miR-451. Only wild-type Ago2 produced the expected product, and this depended upon the presence of Mg2+. No product was produced if we provided a mutant version of the precursor in which a single point mutation disrupted pairing at the cleavage site. Beta elimination and ligation reactions confirmed that cleavage left a free 3' OH terminus as expected of Argonaute proteins. These data strongly support a role for the Ago2 catalytic center in miR-451 maturation. This is perhaps akin to the proposed role of passenger strand cleavage in the maturation of siRISC.

Considered together, our results suggest a model in which miR-451 enters RISC through an alternative biogenesis pathway. Though Drosha cleavage proceeds normally, the Dicer step is skipped and the pre-miRNA is loaded directly into Argonaute. This is surprising, considering prior studies indicating a coupling of Dicer cleavage and RISC loading Chendrimada, T. P. et al. *Nature* 436, 740-4 (2005), Wang, H. W. et al. *Nat Struct Mol Biol* 16, 1148-53 (2009). Such a complex would also lack interactions between the PAZ domain and the 3' end of a conventional Dicer product. Song, J. J. et al. *Nat Struct Biol* 10, 1026-32 (2003), Wang, Y. et al., *Nature* 456, 209-13 (2008). A prior report indicated the ability of RISC to accommodate such species and posited a potential for Ago cleavage in the maturation of canonical microRNAs. Diederichs, S. & Haber, D. A. *Cell* 131, 1097-108 (2007). However, no physiological role for such an activity was demonstrated, and we detect no measurable defects in the processing of canonical miRNAs in Ago2ADH mutants. MiR-451 maturation proceeds with Ago-mediated cleavage producing an intermediate that is further trimmed. While this could occur via either endo- or exo-nucleolytic digestion, the observed distribution of 3' ends, many bearing single non-templated U residues, seems more consistent with the latter model. Though the precise enzymology of this step remains obscure, preliminary studies fail to support roles for Eri-1 or the exosome complex.

5.1.5 Methods

Mouse Strains

Ago2 insertional mutant mouse strains, generated previously were used for mutant analysis, ES cell derivation and reporter analysis. Liu, J. et al. *Science* 305, 1437-41 (2004). Ago1 gene trap strain was generated through germline transmission of Ago1 gene trap ES cells from Bay Genomics (RRR031). Ago2 catalytically inactive mutant knock-in mice were generated through germline transmission of positive ES cell clones targeted with Bacterial artificial chromosome (RP23-56M12) that has been modified with a point mutation D598A in the PIWI domain of Ago2.

Beta-Galactosidase Staining

For whole mount staining, embryos from different stages were dissected together with their extra-embryonic compartments in PBS. Beta galactosidase staining was performed using millipore's staining reagents. X-gal staining was performed overnight at room temperature. For placental sections, whole placentas were first stained for B-gal, sectioned and counterstained with Haematoxylin and Eosin.

Ago2 Mutant Crosses and Embryonic Stem (ES) Cell Derivation

Ago2 mutant phenotype was re-examined combining two insertional alleles for ease of genotyping the homozygous progeny and to take advantage of the Ago2 beta gal reporter allele. Ago2 null ES cells were derived as previously described Nagy, A. et al., Manipulating the Mouse Embryo: A Laboratory Manual (CSHL press, 2003). Null cells were genotyped using primers specific to both insertional alleles. Null cells were genotyped using primers specific to both insertional alleles. Ago2mc allele: forward (GACGGTGAA-GAAGCACAGGAA) (SEQ ID NO: 22), reverse (GGTC-CGATGGGAAAGTGTAGC) (SEQ ID NO: 23). Ago2gt allele: forward (ATGGGATCGGCCATTGAA) (SEQ ID NO: 24), reverse (GAACTCGTCAAGAAGGCG) (SEQ ID NO: 25).

RT-PCR, Western Blot and Immunoprecipitation

Ago2 RT-PCR primers were designed downstream of both insertional alleles: Ago2F: TGTTCCAGCAACCTGTCATC (SEQ ID NO: 26), Ago2R:GATGATCTCCTGTCGGTGCT (SEQ ID NO: 27) Actin primers were used as a normalization control. ActinF: ATGCTCCCCGGGCTGTAT (SEQ ID NO: 28), ActinR: CATAGGAGTCCTTCTGACCCATTC (SEQ ID NO: 29). QRT-PCR was performed using invitrogen superscript III and Applied biosystem cyber green PCR reagent. miRNA levels were measured using Applied Biosystems pri or mature miRNA assays. Ago2 western blot and immunoprecipitation analysis were performed using abnova eif2c2 antibody (M01). P53 western was performed using santa cruz mouse monoclonal antibody (Pab240).

ES-Tetraploid Aggregation

Ago2 null ES cells were injected into tetraploid blastocyst as previously described Nagy, A. & Rossant, J. in Gene Targeting A Practical Approach (ed. Joiner, A. L.) 189-192 (Oxford University Press, 2000). Embryos were transferred to foster mothers and dissected at E12.5. Beta gal stained was performed as described above.

Peripheral Blood Collection and FACS Analysis

Blood was collected from decapitated fetuses (pre-mortem) using heparanized microcapillaries and the CBC count was performed using the hemavet. For FACS analysis, single cells were isolated from neonatal liver, spleen and bone marrow and co-stained with Ter119 and CD71 antibodies (BD) and analyzed on LSRII flow cytometer (BD) as previously described Socolovsky, M. et al, Blood 98, 3261-73 (2001). The Same number of events of each sample were collected according to doublet descrimination gating and analyzed as follows: the ProE cell population was defined by CD71 high/ter119 medium positive events. The ter119 high population was further subdivided into basophilic, late basophilic/polychromatic and orthochromatic/reticulocyte cell populations according to CD71 and FSC parameters to define the subsequent differentiating erythroblasts Liu, Y. et al. Blood 108, 123-33 (2006).

Small RNA Cloning and Bioinformatics Annotation

Total RNA was extracted from E18.5 livers using trizol. Two Small RNA libraries with a size range of 19-30 nt and 30-40 nt were generated using a modified small RNA cloning strategy Aravin, A. & Tuschl, T. FEBS Lett 579, 5830-40 (2005), Pfeffer, S. et al. Nat Methods 2, 269-76 (2005). Briefly, the small RNA fraction was ligated sequentially at its 3'OH and 5'phosphates with synthetic linkers, reverse transcribed and amplified using solexa sequencing primers. Around 7 million reads were generated for each small RNA library. Sequences were then trimmed from the 3' linker, collapsed and mapped to the mouse genome with no mismatches using multiple annotation tracks, namely: UCSC genes, miRNAs and repeats. For this study we used the mirbase database to annotate the cloned miRNAs.

Cell Culture, Plasmids, Transfections and Sensor Assays

Mir-144-451 expression vector was constructed by cloning the genomic cluster into pMSCV retroviral vector. Cre-ER MEFs and ES cells were cultured as previously described 48. Excision of dicer and drosha allele was mediated through tamoxifen treatment (100 nM) for 5 days followed by transient transfection of miR-451 expressing plasmid using lipofectamine (Invitrogen). For in vitro processing assays and northern blots 293T cells were cultured in DMEM+10% FBS and cotransfected using LT-1 Mirus reagent with flag tagged drosha and DGCR8 constructs, myc tagged Ago2 or Ago1 with MSCV-miR144-451 expression vector or myc tagged Ago2 alone. Dual luciferase assays were performed as previously described. For validation of the Ago2 null ES cells, a luciferase plasmid with no artificial site was cotransfected with a perfectly matched siRNA duplex (dharmacon).

Drosha In-Vitro Processing Assays

PCR fragment mapping to miR-451 and mir-144 were amplified out of the human genome with T7 promoter sequence. Pri-451 and Pri-144 RNA transcripts were generated using the genomic PCR product and Ambion's T7 in-vitro transcription kit. Transcripts were gel purified and used in a drosha in-vitro processing assay as previously described Lee, Y. et al. Nature 425, 415-9 (2003), Denli, A. M., et al. Nature 432, 231-5 (2004).

RNA Northern Blot Analysis

RNA was extracted from liver homogenates and Ago2 immunoprecipitates (IPs) using trizol reagent. 10-15 ug of total RNA and ½ of the Wed RNA was run a 20% acrylamide gel and transferred onto a positively charged nylon membrane (hybond). Membranes were crosslinked, prehybridized in ultra-hyb solution (ambion) and hybridized with P32 labeled DNA probes complementary to miR-451 and let-7c. Membranes were washed with 2×SSC, 0.1% SDS and 1×SSC, 0.1% SDS and exposed on a phosphoimager screen overnight.

Ago2 Cleavage Assays and Beta Elimination

Ago2 myc tagged constructs (wt and D797A) were transfected in 293T cells. Lysates were collected after 48 hours, immunoprecipitated using myc agarose beads. The catalysis reaction was carried out on beads using 5' P32 end labeled synthetic pre-miR-451 (dharmacon) as previously described (Liu, J. et al. Science 305, 1437-1441 (2004)). Beta elimination was performed through treating the purified RNA from the Ago2 beads with Sodium periodate for 30 min at room temperature followed by ethanol precipitation. The RNA was resuspended in loading buffer containing TBE and run on a 20% acrylamide gel where the beta elimination reaction occurs.

5.2 Example 2

Design of miR-451 shRNA Structural Mimics

To investigate sequence versus structural requirements for entry into the alternative miRNA biogenesis pathway, we engineered shRNAs as structural mimics of the miR-451 precursor to produce let-7c. This structurally designed shRNA was at least as efficient as the native pre-let-7c in suppressing a GFP or luciferase reporter containing perfect let-7 complementary sites (FIGS. 1A-C) We also designed a miR-451 shRNA mimic targeting p53, here targeting the following site in the p53 mRNA: UCCACUACAAGUACAU-GUGUAA (SEQ ID NO: 6). (FIG. 1D, FIG. 3). Accordingly, an expression construct can therefore be used to efficiently repress p53 in cells by expressing the mir-451 shRNA mimic.

5.2.1 Methods

Testing the functionality of miR-451 mimics was performed using three strategies: (1) cotransfection of let-7-miR-451 mimics, pre-let-7 or let-7 duplex or CTRL RNAs (dharmacon) at a 100 nM concentration with let-7c luciferase reporter construct containing two perfect matching sites in the 3'UTR in HEK293 cells, (2) Similarly, tetracycline inducible Let-7 GFP sensor ES cells containing two perfectly matched sites cotransfected with PE-labeled siRNA and let-7-miR-451 mimics (50 nM) followed by GFP analysis of PE positive cell population using LSRII flow cytometer (BD). GFP sensor was induced using dox (1 ug/ml), (3) For p53 knockdowns, ES cells were transfected with p53 shRNA and p53-miR-451 mimics followed by p53 induction using adriamycin (0.5 ug/ml) within the last 8 hours before harvest. All cells were harvested 48 hours post-transfection.

5.3 Example 3

Expression of miR-451 shRNA Structural Mimics

Figure 7:
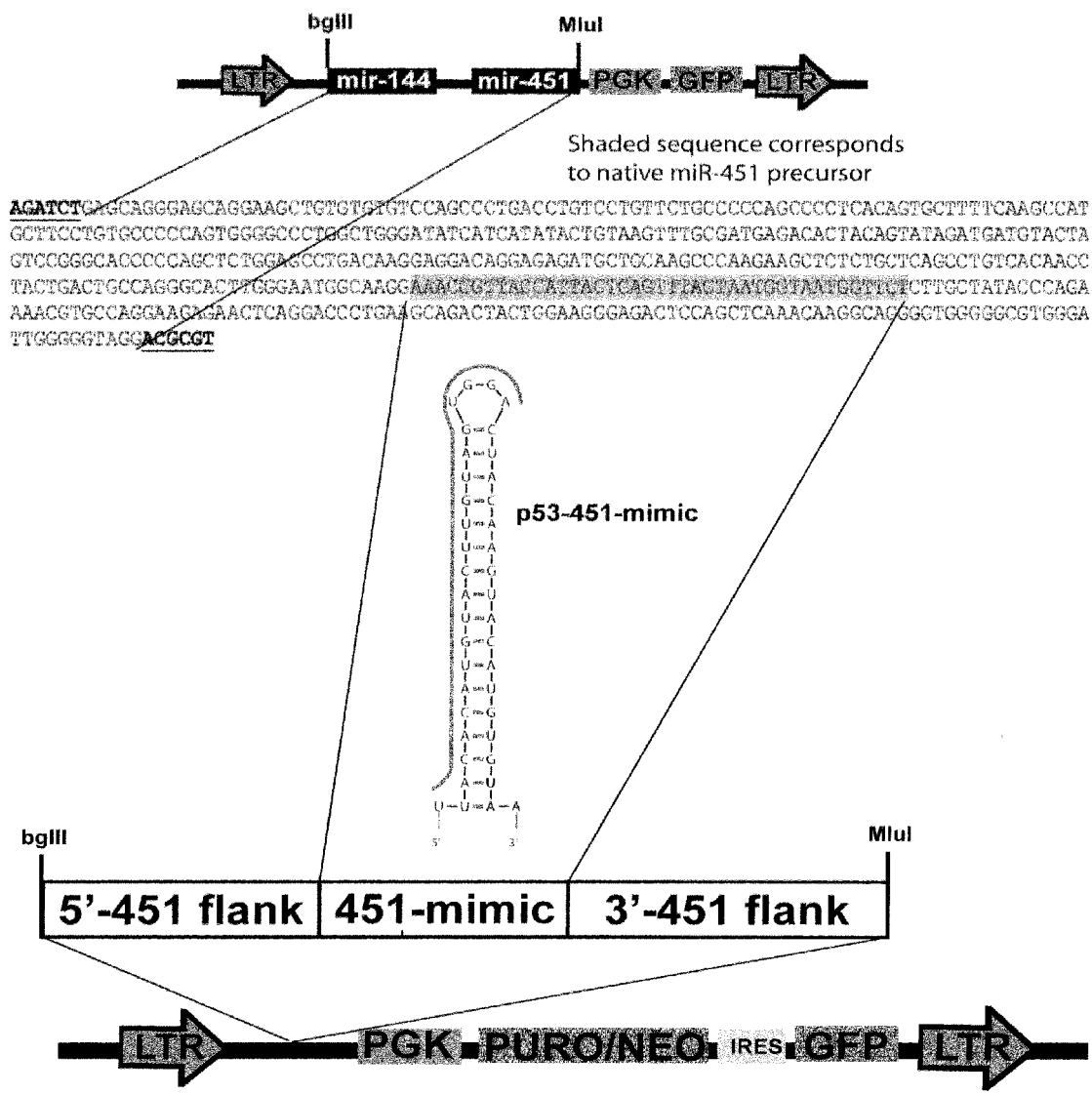

The miR-451 shRNA mimics described in the present application provide a tool with broad applicability for use in RNAi based applications, both for research and in medical applications. As a non-limiting example, miR-451 shRNA mimics designed through the methods of the present application and targeted against particular genes can be used to efficiently repress expression of these genes in mammalian cells, both in culture and in whole animals, including transgenic animals, by expression of the miR-451 shRNA mimic or a precursor molecule for such shRNA. As a further non-limiting example, an MSCV expression plasmid (see for example, FIG. 2, Ex. 1), is used to illustrate how to make expression constructs encoding miR-451 shRNA mimics targeted against p53, based on a miR-451 backbone, The approach is outlined in FIG. 7.

A mir-144-451 fragment cloned in the MluI/BglII site of the Mir-144-451 expression vector (FIGS. 2, 7, Ex. 1) and encompassing the mir-144-455 cluster sequence is amplified out of the human genome. From the amplified fragment, a miR-451 cassette is generated by subcloning a fragment of the mir-144-451 cluster sequence comprising 5' and 3' miR-451 flanking sequences, engineering restriction sites on each of the 5' and 3' ends of that fragment, and subcloning the resulting cassette into an MSCV expression plasmid backbone. An MSCV expression construct encoding a miR-451 shRNA mimic targeted against p53 mRNA is generated by replacing the native miR-451 precursor sequence (FIG. 7, shaded portion; AAACCGTTACCATTACTGAGTTTAG TAATGGTAATGGTT'CT) (SEQ ID NO: 11) with a sequence encoding the mir-451 shRNA mimic. For convenience, it may be desirable to engineer restriction sites into such construct at the 5' and 3' ends of the sequence encoding the miR-451 shRNA mimic, such that an alternative miR-451 shRNA mimic may be easily integrated into the construct by removing the p53 targeted mir-451 shRNA mimic sequence and replacing that sequence with that of the desired targeted miR-451 shRNA mimic.

Generally, so that sufficient cis-acting sequences (and structural determinants) are retained in the expressed miR-451 shRNA mimic to allow for efficient Drosha processing, it is appropriate to include 20 or more bp of miR-451 flanking sequence. In some instances it may be desirable to alter the length of the flanking sequence to optimize expression of the mature miR-451 mimic. Any one of various lengths of either or both 5' and 3' flanking sequence from 5 to 60 bp may be selected and the construct engineered so as to integrate the desired length of flanking sequence into the expression construct cassette. One of skill in the art will appreciate that such lengths of flanking sequence include 5 bp and 60 bp and each intervening integer value between 5 and 60.

The examples are provided to illustrate the general utility of the invention and are not meant to limit the implementation of this approach. The approach illustrated here offers considerable flexibility in use of various expression constructs, alternative vectors and delivery methods, all of which may be routinely optimized for use in particular cells, tissues, organs or animals. For example, expression constructs employing a miR-451 backbone for expression of the mniR-451 shRNA mimics of the invention can be based on any analogous RNA pot II-based expression constructs used for expression of conventional shRNAs, including constructs incorporating inducible/repressible, tissue-specific or developmentally regulated promoters, IRES sites for bicistronic expression, selectable markers, fluorescent markers and RNAi sensors.

5.4 Example 4

MicroRNA-451 Based shRNA Precursors (Drosha Products) are Functional

Figure 8:
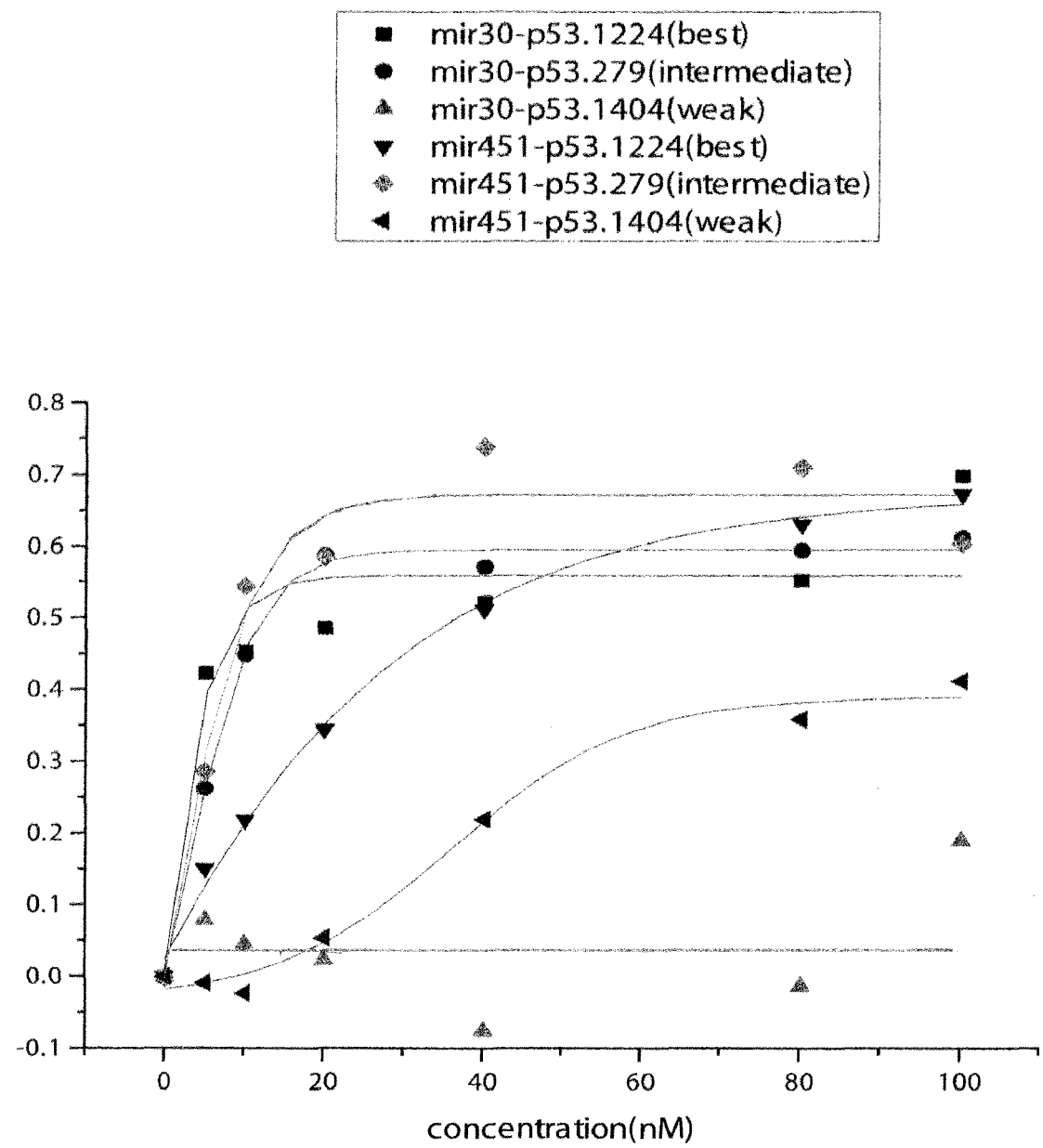

MicroRNA-451 based shRNA precursors (drosha products) are functional in mouse ES cells and manifest a different dose response compared to miR-30 based shRNAs precursor mimics. Without wishing to be bound to, or limited by, any scientific theory, this may suggest different rules in target recognition between the two pathways. Titration curves showing the efficiency of p53 specific shRNAs in miR-451 and miR-30 based mimics were generated (FIG. 8). Three mouse p53 shRNA synthetic RNAs (shp53.1224, shp53.279 and shp53.1404) in miR-451 (40 nt long) and miR-30 (61 nt long) precursor structures were transfected in mouse ES cells. p53 hairpin potency is primarily ranked as best, intermediate and weak according to sensor data described on miR-30 based shRNAs in primary vectors expression system (Fellmann, C. et al. Mol Cell 41, 733-746 (2011)). Concentrations of the p53 shRNAs were titrated using a similar length control shRNA as a control to insure equal amount of the transfected RNA at each concentration of the targeting shRNA. Cells were treated with doxorubicin at final concentration of 500 ng/ml for 8 hrs before harvest. p53 expression level was detected by western blot and quantified based on negative control.

5.5 Example 5

Primary MicroRNA-451 Based shRNA is Functional

Stable expression of the miR-451 mimics using a miR-451 backbone was accomplished as has been described for miR-30. The miR-451 pathway depends on Drosha and Ago2 processing only independently of Dicer. Measurement of knockdown efficiency of miR-451 and miR-30 based primary mimics was performed. (FIGS. 9A and B) p53 Western blots (left panel) followed by quantification (right panel) on primary MEFs infected at low Multiplicity of Infection (MOI) "single copy" and NIH3T3 cells infected at low or high MOI with mouse p53 shRNAs in miR-451 or miR-30 retroviral backbones (MSCV), respectively. Cells were treated with doxorubicin at final concentration of 500 ng/ml for 8 hrs. (FIG. 9C) Renilla luciferase knockdown (left panel) using Four Renilla luciferase shRNAs in miR-451 or miR-30 retroviral backbones (MSCV) were infected in NIH3T3-renilla reporter cells. Renilla luciferase luminescence was normalized to total protein absorbance using BCA measuring assay. GFP expression level (infection efficiency) was shown in the lower graph.

5.6 Example 6

Primary Micro-451 Based shRNAs are Processed Through the Mir-451 Pathway

Figure 10C:
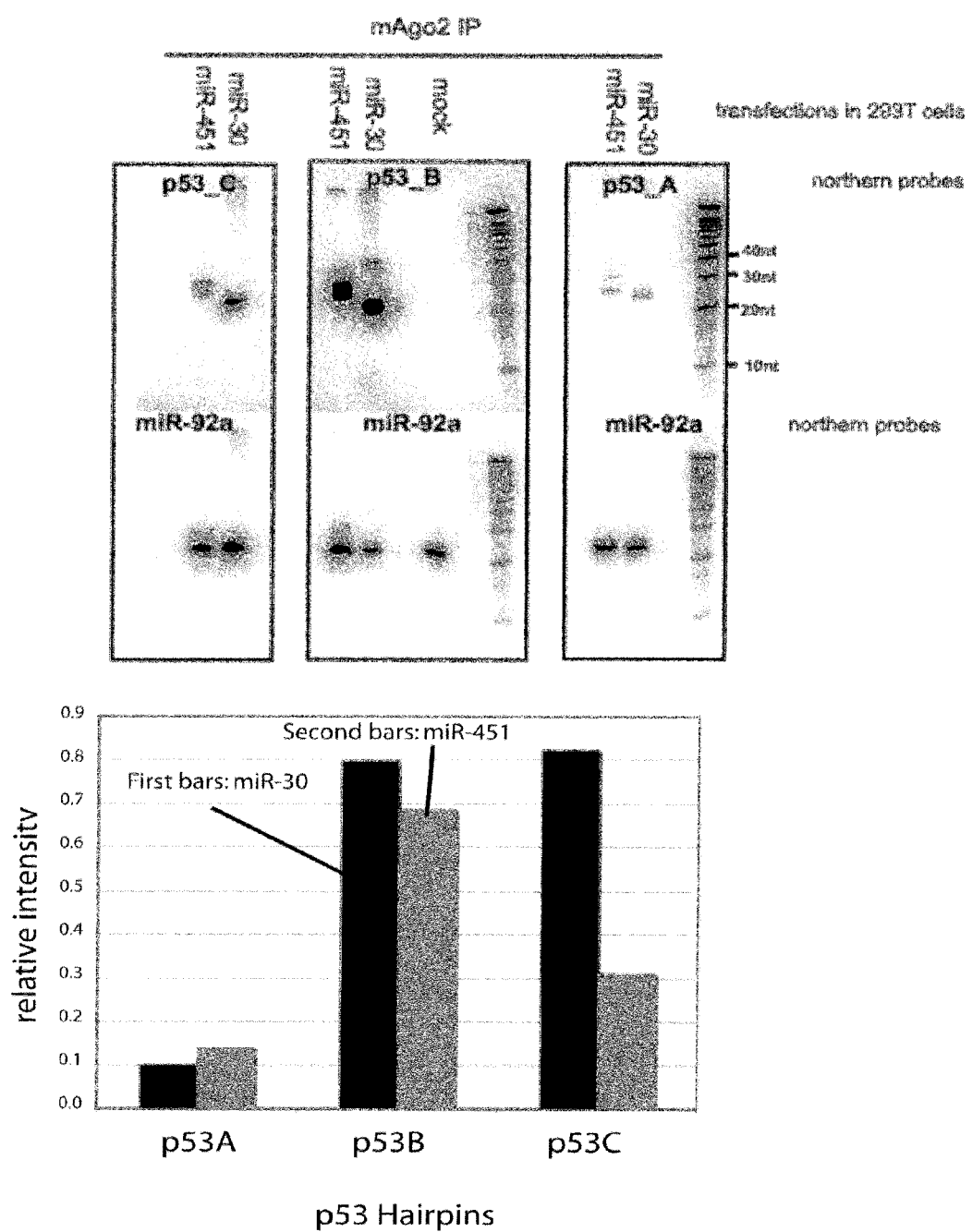
FIG. 10 shows that primary Micro-451 based shRNAs are processed through the miR-451 pathway.
Figure 10D:
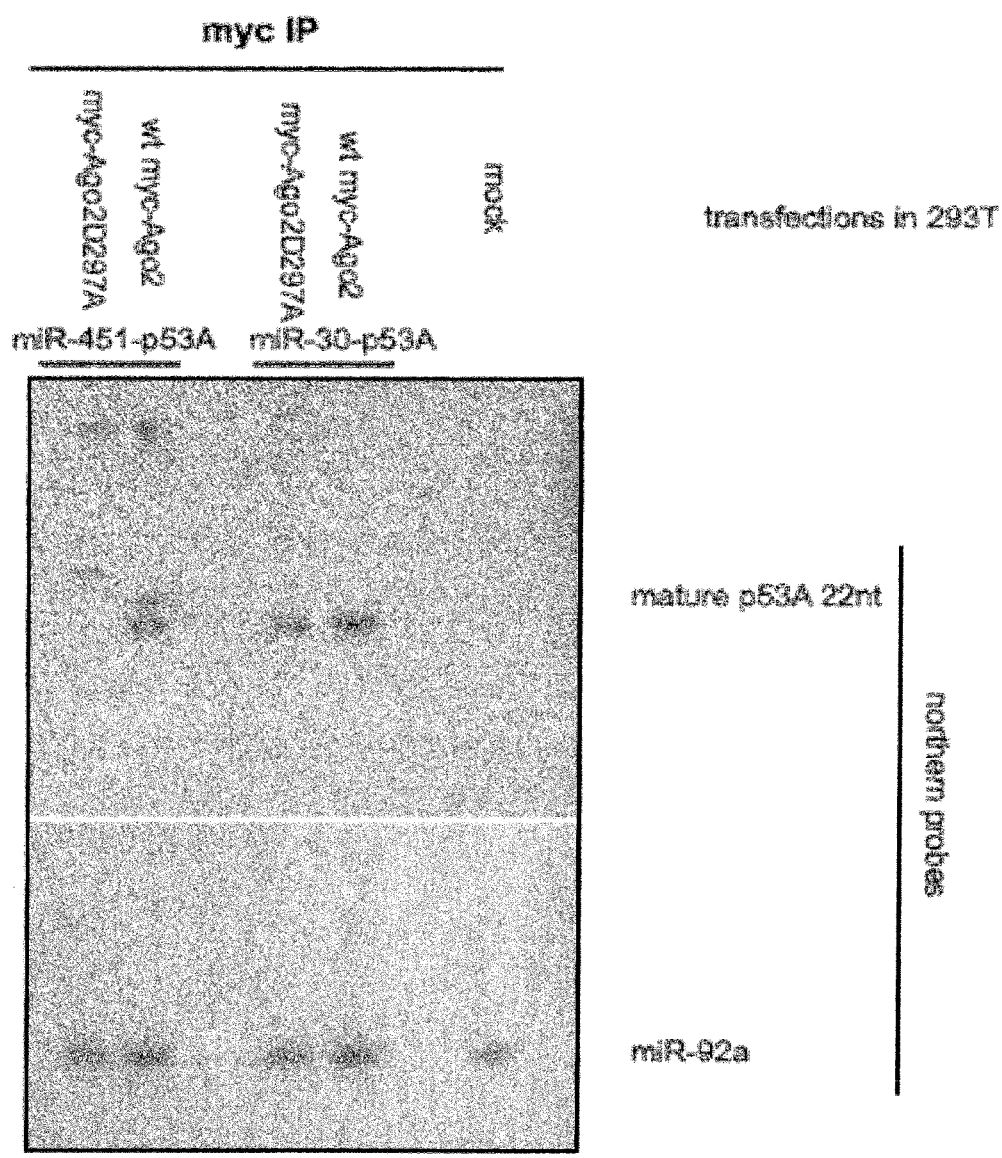

Northern blot analysis from matching RNA samples of the p53 experiments in Example 5 (FIG. 9) was performed using radio labeled probes complementary the mature 22 nt sequences of processed shRNAs. Mature p53 shRNAs were detected in NIH3T3 cells infected with pri-shp53-miR-451 mimics and pri-shp53-miR-30 mimics at low (FIG. 10A) or high (FIG. 10B) MOI. Densitometry quantifications are shown in right panels. (FIGS. 10C and D) Ago2 immunoprecipitation-northern analysis using probes specific to the mature 22 nt sequences of processed primary shRNAs. Pri-shp53-miR-451 and pri-shp53-miR-30 mimics were transfected alone (FIG. 10C) or co-transfected with wild type Ago2 or Ago2 catalytic dead constructs (FIG. 10D) into HEK293T cells. miR-451 mimics were successfully loaded into Ago2 complexes but only processed to their mature form in the wild type protein. Precursor 40 mer mimic accumulated in the catalytically inactive Ago2 (FIG. 10).

5.7 Example 7 miR-451 shRNA Structural Mimic Design Steps 1. choose 22 mer target sequence for example Renilla-shRNA-1 (the first one we tested)

TAGGAATTATAATGCTTATCTA (SEQ ID NO: 30)

2. Reverse complement Renilla 22 mer target sequence

TAGATAAGCATTATAATTCCTA (SEQ ID NO: 31)

3. trim 1 through 18 nt in the reverse complement

TAGATAAGCATTATAATT (SEQ ID NO: 32)

4. reverse complement the trimmed 1-18 to make the stem

AATTATAATGCTTATCTA (SEQ ID NO: 33)

5. join sequences from step 2 and step 4 (the stem) in this order to generate the 40 mer shRNA (SEQ ID NO: 34)
TAGATAAGCATTATAATTCCTA AATTATAATGCTTATCTA

6, To make sure there is a bulge at the first position: If the first nucleotide of shRNA is A or T make sure that the 40$^{th}$ position is C (like endogenous miR-451), if the first position is a C or G, the 40$^{th}$ position should be changed to an A. In this case substitute A at position 40 with C:

(SEQ ID NO: 35)
TAGATAAGCATTATAATTCCTA AATTATAATGCTTATCTC

7. Add flanking regions of endogenous miR-451 and restriction sites for cloning into the destination vector (the minimal backbone depicted here in lowercase letters is about 61 nt and 63 nt long for the 5' and 3' flanks respectively)

(SEQ ID NO: 36)
gaagctctctgctcagcctgtcacaacctactgactgccagggcacttg ggaatggcaaggTAGATAAGCATTATAATTCCTAAATTATAATGCTTAT

CTCtcttgctatacccagaaaacgtgccaggaagagaactcaggaccct gaagcagactactggaa

Restriction sites are either introduced with PCR primers to generate the DNA duxplex for cloning or two complementary oligos are ordered and annealed to make the duplex (FIGS. 11 and 12).

shRNA targeted to other genes can be made in an analogous manner, using a difference sequence of nucleotides to result in the shRNA as described in the various embodiments herein.

5.8 Example 8

Knockdown of Long Non-coding RNA

An example of using HOTAIR shRNA miR-451 and miR-30 mimic design in MSCV expression vector. Target sequences were chosen from siRNAs reported in the literature to target HOTAIR efficiently (Wan, Y. and Chang, H. Y. Cell Cycle 9, 3391-3392 (2010)). When tested in culture, shRNA and siRNAs behave differently. miR-451 based mimics successfully knockdown levels of HOTAIR in one case more efficiently that miR-30 based mimics.

5.9 Example 9 miR-451 Tiling Chip to Generate a miR-451 Based shRNA Library

In order to understand the underlying rules of processing and target recognition of miR-451 mimics, we generated an shRNA tiling chip at one nucleotide step for 10 different genes (p53, bcl2, inch, myc, rpa3, kras, PCNA, GFP, mkate2 and mcherry). 164 mer long synthetic oligo library was generated using Agilent's (Santa Clara, Calif., USA) oligo synthesis platform. The library was then amplified using the constant flanks and cloned in an MSCV destination vector. The library was then transfected in 293T cells and the processing of the shRNAs was analyzed through the generation of small RNA libraries followed by solexa sequencing. The quality of these libraries and their processing efficiency are analysed. Table 1. depicts the efficiency of the sequences recovered in the small RNA library according to input.

TABLE 1

Efficiency of Sequences recovered in the small RNA Library

| | | total number of reads | genome mapping reads | shRNA library mapping reads | miRNA |
|---|---|---|---|---|---|
| miR-451 alignment to predicted CHIP-shRNAs | mature total RNA 19-33 nt | 11,761,255 | 67.59% | 1.16% | 55.12% |
| | Ago2 IP mature 19-33 nt | 15,293,024 | 79.35% | 1.67% | 77.62% |
| | pre-fraction total RNA 40 nt | 2,285,916 | 19.64% | 0.66% | 0.08% |
| miR-30 alignment on predicted 22mer guide strands | mature total RNA | 13,824,773 | 62.81% | 7.42% | 53.08% |
| | Ago2IP mature | 15,640,560 | 64.02% | 9.49% | 61.74% |

What is claimed is:

1. A pre-miR-451 structural mimic consisting of a short hairpin RNA molecule (shRNA) comprising
   (i) a first sequence of 21, 22 or 23 nucleotides fully complementary to a sequence in the coding region of a target gene,
   (ii) a second sequence directly following the first sequence, wherein the second sequence is fully complementary to the sequence of the first 17 or 18 nucleotides counted from the 5' end of the first sequence,
   which structural mimic is DICER independent and requires AGO2 catalysis.

2. The pre-miR-451 structural mimic of claim 1, wherein in the shRNA the last 3 nucleotides of the first sequence form a loop region in the short hairpin molecule.

3. The pre-miR-451 structural mimic of claim 1, wherein in the shRNA the last 4 nucleotides of the first sequence form a loop region in the short hairpin molecule.

4. The pre-miR-451 structural mimic of claim 1, wherein the shRNA has a 1, 2, or 3 nucleotide overhang at its 3' end.

5. The pre-miR-451 structural mimic of claim 1, wherein the shRNA has more than a 3 nucleotide overhang at its 3' end.

6. The pre-miR-451 structural mimic of claim 1, wherein the shRNA has a 1, 2, or 3 nucleotide overhang at its 5' end.

7. The pre-miR-451 structural mimic of claim 1, wherein the shRNA has more than a 3 nucleotide overhang at its 5 end.

8. The pre-miR-451 structural mimic of claim 1, wherein the shRNA has no 3' or 5' overhang.

9. The pre-miR-451 structural mimic of claim 1, wherein the shRNA consists of from 38 to 50 nucleotides.

10. An expression vector comprising a sequence encoding the pre-miR-451 structural mimic according to claim 1 operably linked to an RNA polymerase promoter.

11. A method of attenuating expression of a target gene in a mammalian cell, the method comprising introducing into the mammalian cell an expression vector comprising a sequence encoding a pre-miR-451 structural mimic which is DICER independent and requires AGO2 catalysis and which consists of a short hairpin RNA molecule (shRNA) operably linked to an RNA polymerase promoter, the shRNA comprising:
   (i) a first sequence of 21, 22 or 23 nucleotides fully complementary to a sequence in the coding region of the target gene,
   (ii) a second sequence directly following the first sequence, wherein the second sequence is fully complementary to the sequence of the first 17 or 18 nucleotides counted from the 5' end of the first sequence,
   wherein the shRNA molecule is expressed in the mammalian cell in an amount sufficient to attenuate expression of the target gene in a sequence specific manner, whereby expression of the target gene is inhibited.

12. The method of claim 11, wherein in the shRNA the last 3 nucleotides of the first sequence form a loop region in the short hairpin molecule.

13. The method of claim 11, wherein in the shRNA the last 4 nucleotides of the first sequence form a loop region in the short hairpin molecule.

14. The method of claim 11, wherein the shRNA has a 1, 2, or 3 nucleotide overhang at its 3' end.

15. The method of claim 11, wherein the shRNA has more than a 3 nucleotide overhang at its 3' end.

16. The method of claim 11, wherein the shRNA has a 1, 2, or 3 nucleotide overhang at its 5' end.

17. The method of claim 11, wherein the shRNA has more than a 3 nucleotide overhang at its 5 end.

18. The method of claim 11, wherein the shRNA has no 3' or 5' overhang.

19. The method of claim 11, wherein the shRNA consists of from 38 to 50 nucleotides.

20. The method of claim 11, wherein the expression vector comprises a sequence encoding the pre-miR-451 structural mimic operably linked to an RNA polymerase promoter.

* * * * *

SEQUENCE LISTING

<160> NUMBER OF SEQ ID NOS: 36

<210> SEQ ID NO 1
<211> LENGTH: 40
<212> TYPE: RNA
<213> ORGANISM: Artificial
<220> FEATURE:
<223> OTHER INFORMATION: pre-let-7c-miR-451 mimic hairpin

<400> SEQUENCE: 1
ugagguagua gguuguaugg uuguacaacc uacuaccuca                    40

<210> SEQ ID NO 2
<211> LENGTH: 67
<212> TYPE: RNA
<213> ORGANISM: Mus musculus

<400> SEQUENCE: 2
ugagguagua gguuguaugg uuuagaguua cacccuggga guuaacugua caaccuucua    60
gcuuucc                                                            67

<210> SEQ ID NO 3
<211> LENGTH: 63
<212> TYPE: RNA
<213> ORGANISM: Artificial
<220> FEATURE:
<223> OTHER INFORMATION: p53 hairpin in the mir-30 backbone

<400> SEQUENCE: 3
cccacuacaa guacaugugu aauagugaag ccacagaugu auuacacaug uacuuguagu    60
gga                                                                63

<210> SEQ ID NO 4
<211> LENGTH: 40
<212> TYPE: RNA
<213> ORGANISM: Artificial
<220> FEATURE:
<223> OTHER INFORMATION: p53 hairpin mimicking the miR-451 fold

<400> SEQUENCE: 4
uuacacaugu acuuguagug gacuacaagu acauguguaa                        40

<210> SEQ ID NO 5
<211> LENGTH: 41
<212> TYPE: RNA
<213> ORGANISM: Mus musculus

<400> SEQUENCE: 5
aaaccguuac cauuacugag uuuaguaaug guaacgguuc u                      41

<210> SEQ ID NO 6
<211> LENGTH: 22
<212> TYPE: RNA
<213> ORGANISM: Mus musculus

<400> SEQUENCE: 6
uccacuacaa guacaugugu aa                                          22

<210> SEQ ID NO 7
<211> LENGTH: 61
<212> TYPE: RNA
<213> ORGANISM: Artificial
<220> FEATURE:

<223> OTHER INFORMATION: mir-30 based pre-1224-shp53

<400> SEQUENCE: 7
cacuacaagu acauguguaa uagugaagcc acagauguau uacacaugua cuuguaguga 60
a 61

<210> SEQ ID NO 8
<211> LENGTH: 66
<212> TYPE: RNA
<213> ORGANISM: Mus musculus

<400> SEQUENCE: 8
ggcugggaua ucaucauaua cuguaaguuu gugaugagac acuacaguau agaugaugua 60
cuaguc 66

<210> SEQ ID NO 9
<211> LENGTH: 72
<212> TYPE: RNA
<213> ORGANISM: Mus musculus

<400> SEQUENCE: 9
cuugggaaug gcgaggaaac cguuaccauu acugaguuua guaauggcuaa cgguucucuu 60 gcugcuccca ca 72

<210> SEQ ID NO 10
<211> LENGTH: 462
<212> TYPE: DNA
<213> ORGANISM: Artificial
<220> FEATURE:
<223> OTHER INFORMATION: Fragment of the mir-144-451 cluster sequence
      comprising 5' and 3' miR-451 flanking sequences with engineered
      restriction sites

<400> SEQUENCE: 10
agatctgagc agggagcagg aagctgtgtg tgtccagccc tgacctgtcc tgttctgccc 60
ccagcccctc acagtgcttt tcaagccatg cttcctgtgc ccccagtggg gccctggctg 120
ggatatcatc atatactgta agtttgcgat gagacactac agtatagatg atgtactagt 180
ccgggcaccc ccagctctgg agcctgacaa ggaggacagg agagatgctg caagcccaag 240
aagctctctg ctcagcctgt cacaacctac tgactgccag ggcacttggg aatggcaagg 300
aaaccgttac cattactgag tttagtaatg gtaatggttc tcttgctata cccagaaaac 360
gtgccaggaa gagaactcag gaccctgaag cagactactg gaaggggagac tccagctcaa 420 acaaggcagg ggtgggggcg tgggattggg ggtaggacgc gt 462

<210> SEQ ID NO 11
<211> LENGTH: 41
<212> TYPE: DNA
<213> ORGANISM: Mus musculus

<400> SEQUENCE: 11
aaaccgttac cattactgag tttagtaatg gtaatggttc t 41

<210> SEQ ID NO 12
<211> LENGTH: 23
<212> TYPE: RNA
<213> ORGANISM: Homo sapiens

<400> SEQUENCE: 12
uaaggugcau cuagugcagu uag 23

```
<210> SEQ ID NO 13
<211> LENGTH: 21
<212> TYPE: RNA
<213> ORGANISM: Homo sapiens

<400> SEQUENCE: 13
uaaggugcau cuagugcagu u                                             21

<210> SEQ ID NO 14
<211> LENGTH: 22
<212> TYPE: RNA
<213> ORGANISM: Homo sapiens

<400> SEQUENCE: 14
uaaggugcau cuagugcagu ua                                            22

<210> SEQ ID NO 15
<211> LENGTH: 23
<212> TYPE: RNA
<213> ORGANISM: Homo sapiens

<400> SEQUENCE: 15
uaaggugcau cuagugcagu uag                                           23

<210> SEQ ID NO 16
<211> LENGTH: 22
<212> TYPE: RNA
<213> ORGANISM: Homo sapiens

<400> SEQUENCE: 16
aaggugcauc uagugcaguu ag                                            22

<210> SEQ ID NO 17
<211> LENGTH: 21
<212> TYPE: RNA
<213> ORGANISM: Homo sapiens

<400> SEQUENCE: 17
aggugcaucu agugcaguua g                                             21

<210> SEQ ID NO 18
<211> LENGTH: 22
<212> TYPE: RNA
<213> ORGANISM: Homo sapiens

<400> SEQUENCE: 18
uagcuuauca gacugauguu ga                                            22

<210> SEQ ID NO 19
<211> LENGTH: 21
<212> TYPE: RNA
<213> ORGANISM: Homo sapiens

<400> SEQUENCE: 19
uagcuuauca gacugauguu g                                             21

<210> SEQ ID NO 20
<211> LENGTH: 22
<212> TYPE: RNA
<213> ORGANISM: Homo sapiens

<400> SEQUENCE: 20
uagcuuauca gacugauguu ga                                            22
```

```
<210> SEQ ID NO 21
<211> LENGTH: 21
<212> TYPE: RNA
<213> ORGANISM: Homo sapiens

<400> SEQUENCE: 21
agcuuaucag acugauguug a                                              21

<210> SEQ ID NO 22
<211> LENGTH: 21
<212> TYPE: DNA
<213> ORGANISM: Artificial
<220> FEATURE:
<223> OTHER INFORMATION: Primer for genotyping Ago2 insertional alleles
      in Ago2-null mouse cells.

<400> SEQUENCE: 22
gacggtgaag aagcacagga a                                              21

<210> SEQ ID NO 23
<211> LENGTH: 21
<212> TYPE: DNA
<213> ORGANISM: Artificial
<220> FEATURE:
<223> OTHER INFORMATION: Primer for genotyping Ago2 insertional alleles
      in Ago2-null mouse cells.

<400> SEQUENCE: 23
ggtccgatgg gaaagtgtag c                                              21

<210> SEQ ID NO 24
<211> LENGTH: 18
<212> TYPE: DNA
<213> ORGANISM: Artificial
<220> FEATURE:
<223> OTHER INFORMATION: Primer for genotyping Ago2 insertional alleles
      in Ago2-null mouse cells.

<400> SEQUENCE: 24
atgggatcgg ccattgaa                                                  18

<210> SEQ ID NO 25
<211> LENGTH: 18
<212> TYPE: DNA
<213> ORGANISM: Artificial
<220> FEATURE:
<223> OTHER INFORMATION: Primer for genotyping Ago2 insertional alleles
      in Ago2-null mouse cells.

<400> SEQUENCE: 25
gaactcgtca agaaggcg                                                  18

<210> SEQ ID NO 26
<211> LENGTH: 20
<212> TYPE: DNA
<213> ORGANISM: Artificial
<220> FEATURE:
<223> OTHER INFORMATION: RT-PCT primer for Ago2 insertional alleles in
      mice.

<400> SEQUENCE: 26
tgttccagca acctgtcatc                                                20

<210> SEQ ID NO 27
<211> LENGTH: 20
<212> TYPE: DNA
<213> ORGANISM: Artificial
```

```
<220> FEATURE:
<223> OTHER INFORMATION: RT-PCT primer for Ago2 insertional alleles in
      mice.

<400> SEQUENCE: 27
gatgatctcc tgtcggtgct                                                 20

<210> SEQ ID NO 28
<211> LENGTH: 18
<212> TYPE: DNA
<213> ORGANISM: Artificial
<220> FEATURE:
<223> OTHER INFORMATION: RT-PCT primer for actin in mice.

<400> SEQUENCE: 28
atgctccccg ggctgtat                                                   18

<210> SEQ ID NO 29
<211> LENGTH: 24
<212> TYPE: DNA
<213> ORGANISM: Artificial
<220> FEATURE:
<223> OTHER INFORMATION: RT-PCR primer for actin in mice.

<400> SEQUENCE: 29
cataggagtc cttctgaccc attc                                            24

<210> SEQ ID NO 30
<211> LENGTH: 22
<212> TYPE: DNA
<213> ORGANISM: Artificial
<220> FEATURE:
<223> OTHER INFORMATION: Target Sequence for Renilla-shRNA-1

<400> SEQUENCE: 30
taggaattat aatgcttatc ta                                              22

<210> SEQ ID NO 31
<211> LENGTH: 22
<212> TYPE: DNA
<213> ORGANISM: Artificial
<220> FEATURE:
<223> OTHER INFORMATION: Reverse complement of Renilla-shRNA-1 Sequence

<400> SEQUENCE: 31
tagataagca ttataattcc ta                                              22

<210> SEQ ID NO 32
<211> LENGTH: 18
<212> TYPE: DNA
<213> ORGANISM: Artificial
<220> FEATURE:
<223> OTHER INFORMATION: Trimmed reverse complement of Renilla-shRNA-1
      target sequence

<400> SEQUENCE: 32
tagataagca ttataatt                                                   18

<210> SEQ ID NO 33
<211> LENGTH: 18
<212> TYPE: DNA
<213> ORGANISM: Artificial
<220> FEATURE:
<223> OTHER INFORMATION: Reverse complement of trimmed reverse
      complement of Renilla-shRNA-1 target sequence

<400> SEQUENCE: 33
```

-continued

```
aattataatg cttatcta                                                  18

<210> SEQ ID NO 34
<211> LENGTH: 40
<212> TYPE: DNA
<213> ORGANISM: Artificial
<220> FEATURE:
<223> OTHER INFORMATION: Renilla-shRNA-1 sequence

<400> SEQUENCE: 34
tagataagca ttataattcc taaattataa tgcttatcta                          40

<210> SEQ ID NO 35
<211> LENGTH: 40
<212> TYPE: DNA
<213> ORGANISM: Artificial
<220> FEATURE:
<223> OTHER INFORMATION: Renilla-shRNA-1 sequence with sequence
      substitution

<400> SEQUENCE: 35
tagataagca ttataattcc taaattataa tgcttatctc                          40

<210> SEQ ID NO 36
<211> LENGTH: 164
<212> TYPE: DNA
<213> ORGANISM: Artificial
<220> FEATURE:
<223> OTHER INFORMATION: Renilla-shRNA-1 Sequence with miR451 flanking
      sequences

<400> SEQUENCE: 36
gaagctctct gctcagcctg tcacaaccta ctgactgcca gggcacttgg gaatggcaag    60
gtagataagc attataattc ctaaattata atgcttatct cttgctat acccagaaaa    120 cgtgccagga agagaactca ggaccctgaa gcagactact ggaa                    164
```